US006768007B2

(12) United States Patent
Lee et al.

(10) Patent No.: US 6,768,007 B2
(45) Date of Patent: Jul. 27, 2004

(54) SUBSTITUTED 3',4'-DI-O-CAMPHANOYL-(+)-CIS-KHELLACTONE ANALOGS, COMPOSITIONS THEREOF, AND METHODS FOR USING THEREOF

(75) Inventors: Kuo-Hsiung Lee, Chapel Hills, NC (US); Lan Xie, Beijing (CN); Graham P. Allaway, Darnestown, MD (US); Carl T. Wild, Gaithersburg, MD (US)

(73) Assignees: Panacos Pharmaceuticals, Inc., Gaithersburg, MD (US); The University of North Carolina at Chapel Hill, Chapel Hill, NC (US)

( * ) Notice: Subject to any disclaimer, the term of this patent is extended or adjusted under 35 U.S.C. 154(b) by 73 days.

(21) Appl. No.: 10/096,107

(22) Filed: Mar. 13, 2002

(65) Prior Publication Data

US 2003/0008891 A1 Jan. 9, 2003

Related U.S. Application Data

(60) Provisional application No. 60/275,043, filed on Mar. 13, 2001.

(51) Int. Cl.[7] .................. C07D 213/02; C07D 409/00; C07D 417/00; C07D 335/10; C07D 493/00

(52) U.S. Cl. ............... 546/194; 546/196; 546/202; 549/27; 549/282

(58) Field of Search ............... 549/282, 27; 546/194, 546/196, 202

(56) References Cited

U.S. PATENT DOCUMENTS

| | | | | |
|---|---|---|---|---|
| 5,612,341 | A | 3/1997 | Lee et al. | 514/253 |
| 5,637,589 | A | 6/1997 | Lee et al. | 514/291 |
| 5,726,204 | A | 3/1998 | Lee et al. | 514/455 |
| 5,847,165 | A | * 12/1998 | Lee et al. | 549/282 |
| 6,319,929 | B1 | 11/2001 | Lee et al. | 514/291 |

OTHER PUBLICATIONS

Chilin, A., et al., "Synthesis and Biological Activity of (Hydroxymethyl)–and (Diethylaminomethyl)benzopsoralens," *J. Med. Chem.* 42:2936–2945, The American Chemical Society (1999).

Dalgleish, A.G., et al., "The CD4 (T4) antigen is an essential component of the receptor for the AIDS retrovirus," *Nature* 312:763–767, Macmillan Journals Ltd. (1984).

Doucet, C., et al., "6–Substituted 2–Oxo–2H–1–benzopyran–3–carboxylic Acid as a Core Structure for Specific Inhibitors of Human Leukocyte Elastase," *J. Med. Chem.* 42:4161–4171, The American Chemical Society (1999).

Hashimoto, F., et al., "Anti–AIDS Agents–XXVII. Synthesis and Anti–HIV Activity of Betulinic Acid and Dihydrobetulinic Acid Derivatives," *Bioorg. Med. Chem.* 5:2133–2143, Pergamon Press (1997).

Huang, L., et al., "3', 4'–Di–O–(–)–camphanoyl–(+)–cis–khellactone and Related Compounds: A New Class of Potent Anti–HIV Agents," *Bioorg. Med. Chem. Lett.* 4:593–598, Pergamon Press (1994).

Kashiwada, Y., et al., "Betulinic Acid and Dihydrobetulinic Acid Derivatives as Potent Anti–HIV Agents," *J. Med. Chem.* 39:1016–1017, The American Chemical Society (1996).

Lee, K.–H., et al., "Recent advances in the discovery and development of plant–derived natural products and their analogs as anti–HIV agents," *Pure Appl. Chem.* 71:1045–1051, Blackwell Science (1999).

(List continued on next page.)

*Primary Examiner*—Alan L. Rotman
*Assistant Examiner*—Raymond Covington
(74) *Attorney, Agent, or Firm*—Sterne, Kessler, Goldstein & Fox P.L.L.C.

(57) ABSTRACT

3',4'-di-O-camphanoyl-(+)-cis-khellactone analogs according to the present invention have been found to have anti-HIV activity. The compounds of the present invention have the following formula:

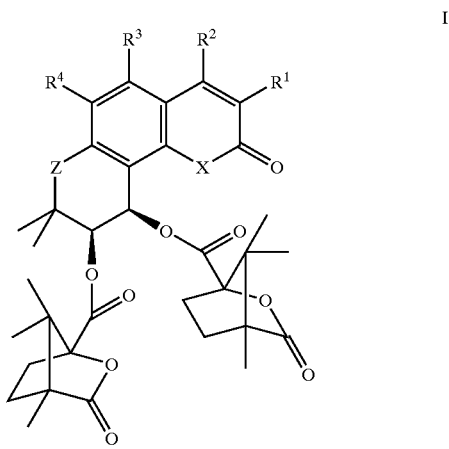

or a pharmaceutically acceptable salt, ester or prodrug thereof, wherein $R^1$, $R^2$, $R^3$, $R^4$, X, and Z are set in the specification. The invention is also directed to pharmaceuticals compositions comprising one or more compounds of Formula I, optionally further comprising one or more antiviral agents or immunostimulating agents. Further, the invention is directed to the use of compounds of Formula I for the inhibition of a retroviral infection in cells or tissue of an animal, for the treatment of a patient suffering from a retroviral-related pathology, for the prevention of transmission of HIV infection from an HIV infected pregnant woman to a fetus, and for the prevention of transmission of HIV infection during sexual intercourse.

23 Claims, No Drawings

OTHER PUBLICATIONS

Lee, K.–H., "6. Highlights of Research on Plant–Derived Natural Products and Their Analogs with Antitumor, Anti–HIV, and Antifungal Activity," in: *Biologically Active Natural Product: Pharmaceuticals*, Cutler, S.J. and Culter, H.G., eds., CRC Press, Boca Raton, Florida, pp. 73–94 (1999).

Schade, B., et al., "Deactivation Behavior and Excited–State Properties of (Coumarin–4–yl)methyl Derivatives. 1. Photocleavage of (7–Methoxycoumarin–4–yl) methyl–Caged Acids with Fluorescence Enhancement," *J. Org. Chem.* 64:9109–9117, The American Chemical Society (1999).

Xia, Y., et al., "Asymmetric Solid–Phase Synthesis of (3'R, 4'R)–Di–O–cis–acyl 3–Carboxyl Khellactones," *Org. Lett.* 1:2113–2115, The American Chemical Society (1999).

Xie, L., et al., "Asymmetric Synthesis of 3',4'–Di–O–(–)–Camphanoyl–(+)–Cis–Khellactone (DCK), A Potent Anti–HIV Agent," *Tetrahedron Lett.* 36:4529–4532, Pergamon Press (1995).

Xie, L., et al., "Anti–AIDS Agents 37. Synthesis and Structure–Activity Relationships of (3'R,4'R)–(+)–cis–Khellactone Derivatives as Novel Potent Anti–HIV Agents," *J. Med. Chem.* 42:2662–2672, The American Chemical Society (1999).

Xie, L., "Design, Synthesis, and Biological Evaluation of (+)–Cis–Khellactone Derivatives as Potent Anti–HIV Agents," Doctoral Dissertation, University of North Carolina at Chapel Hill, Chapel Hill, North Carolina, pp. 1–163 (1999).

Xie, L., et al., "Anti–AIDS Agents. 42. Synthesis and Anti–HIV Activity of Disubstituted (3'R,4'R)–3', 4'–Di–O–(S)–camphanoyl–(+)–cis–khellactone Analogues," *J. Med. Chem.* 44:664–671, The American Chemical Society (Published Online Jan. 2001).

Xie, L. et al., "Anti–AIDS Agents. Part 47: Synthesis and Anti–HIV Activity of 3–Substituted 3',4'–Di–O–(S)–camphanoyl–(3'R,4'R)–(+)–cis–khellactone Derivatives," *Bioorg. Med. Chem. Lett.* 11:2291–2293, Pergamon Press (Sep. 2001).

Yang, Z.–Y., et al., "Anti–AIDS Agents Part 41: Synthesis and Anti–HIV Activity of 3',4'–Di–o–(–)–camphanoyl–(+)–cis–khellactone (DCK) Lactam Analogues," *Bioorg. Med. Chem. Lett.* 10:1003–1005, Pergamon Press (May 2000).

* cited by examiner

SUBSTITUTED 3',4'-DI-O-CAMPHANOYL-(+)-CIS-KHELLACTONE ANALOGS, COMPOSITIONS THEREOF, AND METHODS FOR USING THEREOF

This application claims the priority benefit under 35 U.S.C. § 119 of U.S. Provisional Appl. No. 60/275,043, filed Mar. 13, 2001, the entirety of which is incorporated by reference herein.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds under grant AI-33066. The U.S. Government has certain rights in this invention.

BACKGROUND OF THE INVENTION

1. Field of the Invention

The present invention relates to novel 3',4'-di-O-camphanoyl-(+)-cis-khellactone analogs, and the use of such compounds as pharmaceuticals.

2. Background Art

Retroviruses are small, single-stranded positive-sense RNA viruses. A retroviral particle comprises two identical single-stranded positive sense RNA molecules. Their genome contains, among other things, the sequence of the RNA-dependent DNA polymerase, also known as reverse transcriptase. Many molecules of reverse transcriptase are found in close association with the genomic RNA in the mature viral particles. Upon entering a cell, this reverse transcriptase produces a double-stranded DNA copy of the viral genome, which is then inserted into the chromatin of a host cell. Once inserted, the viral sequence is called a provirus. Retroviral integration is directly dependent upon viral proteins. Linear viral DNA termini (the LTRs) are the immediate precursors to the integrated proviral DNA. There is a characteristic duplication of short stretches of the host's DNA at the site of integration.

Progeny viral genomes and mRNAs are transcribed from the inserted proviral sequence by host cell RNA polymerase in response to transcriptional, regulatory signals in the terminal regions of the proviral sequence, the long terminal repeats, or LTRs. The host cell's protein production machinery is used to produce viral proteins, many of which are inactive until processed by virally encoded proteases. Typically, progeny viral particles bud from the cell surface in a non-lytic manner. Retroviral infection does not necessarily interfere with the normal life cycle of an infected cell or organism. However, neither is it always benign with respect to the host organism. While most classes of DNA viruses can be implicated in tumorigenesis, retroviruses are the only taxonomic group of RNA viruses that are oncogenic. Various retroviruses, such as the Human Immunodeficiency Virus (HIV), which is the etiological agent responsible for acquired immune deficiency syndrome (AIDS) in humans, are also responsible for several very unusual diseases of the immune system of higher animals.

Human Immunodeficiency Virus (HIV) is a member of the lentiviruses, a subfamily of retroviruses. Many retroviruses are well-known carcinogens. HIV per se is not known to cause cancer in humans or other animals, but it does present a formidable challenge to the host. The viral genome contains many regulatory elements which allow the virus to control its rate of replication in both resting and dividing cells. Most importantly, HIV infects and invades cells of the immune system; it breaks down the body's immune system and renders the patient susceptible to opportunistic infections and neoplasms. The immune defect appears to be progressive and irreversible, with a high mortality rate that approaches 100% over several years.

HIV-1 is trophic and cytopathic for T4 lymphocytes, cells of the immune system which express the cell surface differentiation antigen CD4, also known as OKT4, T4 and leu3. The viral tropism is due to the interactions between the viral envelope glycoprotein, gp120, and the cell-surface CD4 molecules (Dalgleish et al., Nature 312:763–767 (1984)). These interactions not only mediate the infection of susceptible cells by HIV, but are also responsible for the virus-induced fusion of infected and uninfected T cells. This cell fusion results in the formation of giant multinucleated syncytia, cell death, and progressive depletion of CD4 cells in HIV-infected patients. These events result in HIV-induced immunosuppression and its subsequent sequelae, opportunistic infections and neoplasms.

In addition to CD4+ T cells, the host range of HIV includes cells of the mononuclear phagocytic lineage (Dalgleish et al., supra), including blood monocytes, tissue macrophages, Langerhans cells of the skin and dendritic reticulum cells within lymph nodes. HIV is also neurotropic, capable of infecting monocytes and macrophages in the central nervous system causing severe neurologic damage. Macrophage/monocytes are a major reservoir of HIV. They can interact and fuse with CD4-bearing T cells, causing T cell depletion and thus contributing to the pathogenesis of AIDS.

Considerable progress has been made in the development of drugs for HIV-1 therapy during the past few years. There are now 14 drugs approved for use in the U.S., including six nucleoside analog reverse transcriptase inhibitors (AZT, 3TC, ddI, ddC, D4T, and abacavir), three non-nucleoside RT inhibitors (nevirapine, delavirdine, and efavirenz) and five protease inhibitors (saquinavir, ritonavir, indinavir, nelfinavir, and amprenavir). Combinations of these drugs are particularly effective and can reduce levels of viral RNA to undetectable levels in the plasma and slow the development of viral resistance, with resulting improvements in patient health and life span.

Despite these advances, there are still problems with the currently available drug regimens. Many of the drugs exhibit severe toxicities, have other side-effects (e.g., fat redistribution) or require complicated dosing schedules that reduce compliance and thereby limit efficacy. Resistant strains of HIV often appear over extended periods of time even on combination therapy. The high cost of these drugs is also a limitation to their widespread use, especially outside of developed countries.

There is still a major need for the development of additional drugs to circumvent these issues. Ideally these would target different stages in the viral life cycle, adding to the armamentarium for combination therapy, and exhibit minimal toxicity, yet have lower manufacturing costs.

Previously, suksdorfin, i.e., (3'R,4'R)-3'-acetoxy-4'-isovaleryloxy-(+)-cis-khellactone, was isolated as an anti-HIV principle from the fruit of Lomatium suksdorfii. Suksdorfin exhibited inhibitory activity against HIV-1 replication in H9 lymphocyte cells with $EC_{50}$ value of 1.3 μM, and therapeutic index (TI) value of 140. The discovery of suksdorfin led to the syntheses of khellactone derivatives and led to a second lead compound 3',4'-di-O-(S)-(−)-camphanoyl-(3'R,4'R)-(+)-cis-khellactone (DCK), which showed extremely potent anti-HIV activity with $EC_{50}$ value of $2.56 \times 10^{-4}$ μM and a TI value of 136,719 (Xie, L. et al., J. Med. Chem. 42:2662–2672 (1999)).

Xie, L. et al. describe that alkyl and O-alkyl substituents at the 3-, 4-, and 5-positions of DCK produce derivatives with potent anti-HIV activity (J. Med. Chem. 42:2662–2672 (1999)). DCK derivatives are also described in U.S. Pat. Nos. 5,847,165, 5,637,589, 5,726,204, and 5,612,341.

A need continues to exist for compounds which possess anti-HIV activity with improved biodistribution properties. There is also a need for safe and effective compounds that can be topically applied to vaginal or other mucosa to prevent HIV infection between individuals.

BRIEF SUMMARY OF THE INVENTION

The present invention provides novel 3',4'-di-O-camphanoyl-(+)-cis-khellactone analogs of Formula I:

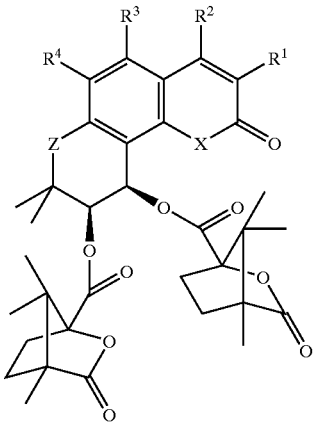

or pharmaceutically acceptable salts, esters, or prodrugs thereof; wherein $R^1$ and $R^4$ are independently selected from the group consisting of hydrogen, halogen, hydroxy, alkyl, alkoxy, acyloxy, amino, monoalkylamino, dialkylamino, trifluoromethyl, trifluoromethoxy, —$CH_2CONH$-alkyl, and $C_{1-4}$ alkyl substituted with one or more of halogen, trifluoromethyl, cyano, hydroxy, amino, monoalkylamino, or dialkylamino, wherein at least one of $R^1$ or $R^4$ is a substituted $C_{1-4}$ alkyl group;

$R^2$ and $R^3$ are independently selected from the group consisting of hydrogen, halogen, hydroxy, alkyl, alkoxy, acyloxy, amino, monoalkylamino, dialkylamino, trifluoromethyl, trifluoromethoxy, phenyl, and —$CH_2CONH$-alkyl;

X and Z are independently selected from the group consisting of O, S and NH; and where the configurations at 3' and 4' can be (R) or (S).

The present invention also provides novel 3',4'-di-O-camphanoyl-(+)-cis-khellactone compounds of Formula II:

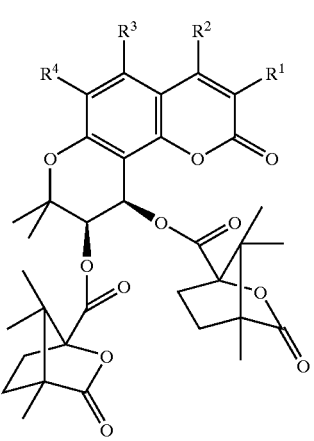

or pharmaceutically acceptable salts, esters, or prodrugs thereof; wherein $R^1$ and $R^4$ are independently selected from the group consisting of hydrogen, halogen, hydroxy, alkyl, alkoxy, acyloxy, amino, monoalkylamino, dialkylamino, trifluoromethyl, trifluoromethoxy, —$CH_2CONH$-alkyl, and $C_{1-4}$ alkyl substituted with one or more of halogen, trifluoromethyl, cyano, hydroxy, amino, monoalkylamino, or dialkylamino, wherein at least one of $R^1$ or $R^4$ is a substituted $C_{1-4}$ alkyl group;

$R^2$ and $R^3$ are independently selected from the group consisting of hydrogen, halogen, hydroxy, alkyl, alkoxy, acyloxy, amino, monoalkylamino, dialkylamino, trifluoromethyl, trifluoromethoxy, phenyl, and —$CH_2CONH$-alkyl; and where the configurations at 3' and 4' can be (R) or (S).

The present invention also provides pharmaceutical compositions, comprising one or more compounds of Formula I, and a pharmaceutically acceptable carrier or diluent. One or more additional pharmaceutically active compounds can also be included in these compositions.

The compounds of Formula I are useful as anti-retroviral agents. Therefore, the present invention provides methods for inhibiting a retroviral infection in cells or tissue of an animal, comprising administering an effective retroviral inhibiting amount of a compound of Formula I. A preferred embodiment provides a method for treating a patient suffering from a retroviral-related pathology, comprising administering to said subject a retroviral inhibiting effective amount of a pharmaceutical composition that includes a compound of Formula I.

The 3',4'-di-O-camphanoyl-(+)-cis-khellactone analogs of Formula I can be used in a combination therapy with one or more anti-viral agents. Thus, the present invention provides a method of treating a patient suffering from a retroviral-related pathology, comprising administering to said patient a retroviral inhibiting effective amount of a compound of Formula I in combination with one or more anti-viral agents. Preferably, the anti-viral agent is approved for use for HIV-therapy in the U.S.

The present invention also provides a method of preventing transmission of HIV infection between individuals. In particular, the present invention provides a method of preventing transmission of HIV infection from an HIV infected pregnant woman to a fetus, comprising administering to said woman and/or said fetus a retroviral inhibiting effective amount of one or more compounds of Formula I during pregnancy or immediately prior to, at, or subsequent to birth.

Further, the present invention provides a method of preventing transmission of HIV infection during sexual intercourse, comprising applying a retroviral inhibiting effective amount of a topical composition including one or more compounds of Formula I to vaginal or other mucosa prior to sexual intercourse.

Furthermore, the present invention provides a method for making compounds of Formula I.

Additional embodiments and advantages of the invention will be set forth in part in the description as follows, and in part will be obvious from the description, or may be learned by practice of the invention. The embodiments and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE INVENTION

The 3',4'-di-O-camphanoyl-(+)-cis-khellactone analogs of the present invention have the general Formula I:

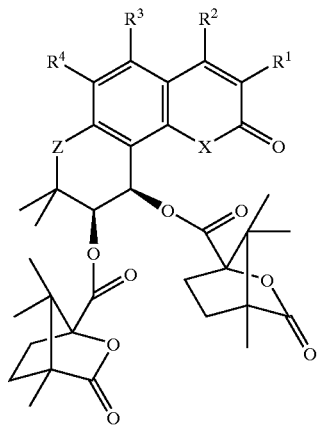

I or a pharmaceutically acceptable salt, ester, or prodrug thereof; wherein $R^1$ and $R^4$ are independently selected from the group consisting of hydrogen, halogen, hydroxy, alkyl, alkoxy, amino, monoalkylamino, dialkylamino, trifluoromethyl, trifluoromethoxy, —$CH_2CONH$-alkyl, and a $C_{1-4}$ alkyl substituted with one or more of halogen, trifluoromethyl, cyano, hydroxy, amino, monoalkylamino, or dialkylamino, wherein at least one of $R^1$ or $R^4$ is a substituted $C_{1-4}$ alkyl group;

$R_2$ and $R^3$ are independently selected from the group consisting of hydrogen, halogen, hydroxy, alkyl, alkoxy, acyloxy, amino, monoalkylamino, dialkylamino, trifluoromethyl, trifluoromethoxy, phenyl, and —$CH_2CONH$-alkyl;

X and Z are independently selected from the group consisting of O, S and NH; and where the configurations at 3' and 4' can be (R) or (S).

Useful compounds included in the general Formula I are 3',4'-di-O-camphanoyl-(+)-cis-khellactone compounds of Formula II:

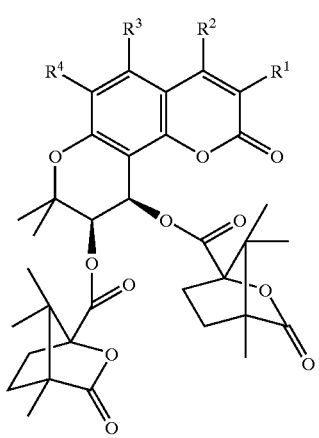

II or pharmaceutically acceptable salts, esters, or prodrugs thereof; wherein $R^1$ and $R^4$ are independently selected from the group consisting of hydrogen, halogen, hydroxy, alkyl, alkoxy, acyloxy, amino, monoalkylamino, dialkylamino, trifluoromethyl, trifluoromethoxy, —$CH_2CONH$-alkyl, and $C_{1-4}$ alkyl substituted with one or more of halogen, trifluoromethyl, cyano, hydroxy, amino, monoalkylamino, or dialkylamino, wherein at least one of $R^1$ or $R^4$ is a substituted $C_{1-4}$ alkyl group;

$R^2$ and $R^3$ are independently selected from the group consisting of hydrogen, halogen, hydroxy, alkyl, alkoxy, acyloxy, amino, monoalkylamino, dialkylamino, trifluoromethyl, trifluoromethoxy, phenyl, and —$CH_2CONH$-alkyl; and where the configurations at 3' and 4' can be (R) or (S).

The $C_{1-4}$ alkyl group can be a straight-chain or a branched alkyl group.

Preferred compounds of the present invention are those where $R^3$ and $R^4$ are hydrogen, and $R^1$ is a substituted $C_{1-4}$ alkyl group. Another group of preferred compounds are those where $R^1$ and $R^3$ are hydrogen, and $R^4$ is a substituted $C_{1-4}$ alkyl group. Preferably, the $C_{1-4}$ alkyl group is methyl or ethyl. Preferably, $R^2$ is hydrogen or $C_{1-4}$ alkyl, preferably methyl. Preferably, $R^1$ and $R^4$ are hydroxymethyl or halomethyl groups or esters thereof.

Suitable substituted alkyl groups include bromomethyl, dibromomethyl, hydroxymethyl, dihydroxymethyl, acetoxymethyl, (dimethylphosphate)methyl, aminomethyl, diethylaminoethyl, and dimethylaminomethyl.

Ester groups are preferably of the type which are relatively readily hydrolyzed under physiological conditions. Examples of pharmaceutically acceptable esters of the compounds of the invention include $C_{1-6}$ alkyl esters wherein the alkyl group is a straight or branched chain. Acceptable esters also include $C_{5-7}$ cycloalkyl esters as well as arylalkyl esters, such as, but not limited to benzyl. $C_{1-4}$ alkyl esters are preferred. Preferably the esters are selected from the group consisting of alkylcarboxylic acid esters, such as acetic acid esters, and mono- or dialkylphosphate esters, such as methylphoshate ester or dimethylphosphate ester. Esters of the compounds of the present invention can be prepared according to conventional methods.

Preferably, the configurations at 3' and 4' are both (R). Also, preferably the O-camphanoyl group is O-(S)-(−)-camphanoyl.

Useful compounds include:

(3'R,4'R)-3',4'-di-O-(S)-(−)-camphanoyl-3-bromomethyl-(+)-cis-khellactone;

(3'R,4'R)-3',4'-di-O-(S)-(−)-camphanoyl-3-dibromomethyl-(+)-cis-khellactone;

(3'R,4'R)-3',4'-di-O-(S)-(−)-camphanoyl-3-acetoxymethyl-(+)-cis-khellactone;

(3'R,4'R)-3',4'-di-O-(S)-(−)-camphanoyl-3-hydroxymethyl-(+)-cis-khellactone;

(3'R,4'R)-3',4'-di-O-(S)-(−)-camphanoyl-3-bromomethyl-4-methyl-(+)-cis-khellactone;

(3'R,4'R)-3',4'-di-O-(S)-(−)-camphanoyl-3-acetoxymethyl-4-methyl-(+)-cis-khellactone;

(3'R,4'R)-3',4'-di-O-(S)-(−)-camphanoyl-3-hydroxymethyl-4-methyl-(+)-cis-khellactone;

(3'R,4'R)-3',4'-di-O-(S)-(−)-camphanoyl-6-bromomethyl-(+)-cis-khellactone;

(3'R,4'R)-3',4'-di-O-(S)-(−)-camphanoyl-6-dibromomethyl-4-methyl-(+)-cis-khellactone;

(3'R,4'R)-3',4'-di-O-(S)-(−)-camphanoyl-6-bromomethyl-4-methyl-(+)-cis-khellactone;

(3'R,4'R)-3',4'-di-O-(S)-(−)-camphanoyl-6-acetoxymethyl-4-methyl-(+)-cis-khellactone;

(3'R,4'R)-3',4'-di-O-(S)-(−)-camphanoyl-6-hydroxymethyl-4-methyl-(+)-cis-khellactone;

(3'R,4'R)-3',4'-di-O-(S)-(−)-camphanoyl-6-(dimethylphosphate)methyl-4-methyl-(+)-cis-khellactone;

(3'R,4'R)-3',4'-di-O-(S)-(−)-camphanoyl-3-aminomethyl-(+)-cis-khellactone;

(3'R,4'R)-3',4'-di-O-(S)-(−)-camphanoyl-6-aminomethyl-4-methyl-(+)-cis-khellactone; and (3'R,4'R)-3',4'-di-O-(S)-(−)-camphanoyl-3-diethylaminomethyl-(+)-cis-khellactone as well as pharmaceutically acceptable salts and esters thereof.

Useful halo or halogen groups include fluorine, chlorine, bromine and iodine.

Useful alkyl groups include straight-chained and branched $C_{1-10}$ alkyl groups, more preferably $C_{1-6}$ alkyl groups, more preferably $C_{1-4}$ alkyl groups. Typical $C_{1-10}$ alkyl groups include methyl, ethyl, propyl, isopropyl, butyl, sec-butyl, 3-pentyl, hexyl and octyl groups.

Useful alkoxy groups include oxygen substituted by one of the $C_{1-10}$ alkyl groups mentioned above.

Useful acyloxy groups are any $C_{1-6}$ acyl (alkanoyl) attached to an oxy (—O—) group, e.g., acetoxy, propionyloxy, butanoyloxy, pentanoyloxy, hexanoyloxy and the like.

An amino group is —$NH_2$.

Useful monoalkylamino and dialkylamino groups are —$NHR^5$ and —$NNR^5R^6$, wherein $R^5$ and $R^6$ are $C_{1-10}$ alkyl groups.

Also, included within the scope of the present invention are the non-toxic pharmaceutically acceptable salts of the compounds of the present invention. These salts can be prepared in situ during the final isolation and purification of the compounds or by separately reacting the purified compound in its free base form with a suitable organic or inorganic acid and isolating the salt thus formed. Examples of pharmaceutically acceptable salts include inorganic and organic acid addition salts such as hydrochloride, hydrobromide, phosphate, sulfate, bisulfate, nitrate, citrate, lactate, tartrate, maleate, fumarate, mandelate, acetate, dichloroacetate, oxalate, valerate, oleate, palmitate, stearate, laureate, borate, benzoate, tosylate, succinate, naphthylate, mesylate, and the like. These may include cations based on the alkali and alkali earth metals, such as sodium, lithium, potassium, calcium, magnesium, and the like, as well as nontoxic ammonium, quaternary ammonium and amine cations including, but not limited to ammonium, tetramethylammonium, tetraethylammonium, methylamine, dimethylamine, trimethylamine, ethylamine, and the like.

Certain compounds within the scope of Formulae I and II are derivatives referred to as "prodrugs". The expression "prodrug" refers to compounds that are rapidly transformed in vivo by an enzymatic or chemical process, to yield the parent compound of the above formulas, for example, by hydrolysis in blood. A thorough discussion is provided by Higuchi, T. and V. Stella in *Pro-drugs as Novel Delivery Systems,* Vol. 14, A.C.S. Symposium Series, and in *Bioreversible Carriers in Drug Design,* Ed. Edward B. Roche, American Pharmaceutical Association, Pergamon Press, 1987. Useful prodrugs are esters of compounds of Formulae I and II, wherein at least one of $R^1$ or $R^4$ is a lower alkyl group substituted with one or more hydroxy or halo groups, with a suitable acid. Suitable acids include, e.g., carboxylic acids, sulfonic acids, phosphoric acid or lower alkyl esters thereof, and phosphonic acid or lower alkyl esters thereof. For example, suitable carboxylic acids include alkylcarboxylic acids, such as acetic acid, arylcarboxylic acids and arylalkylcarboxylic acids. Suitable sulfonic acids include alkylsulfonic acids, arylsulfonic acids and arylalkylsulfonic acids. Suitable phosphoric and phosphonic acid esters are methyl or ethyl esters.

Further useful prodrugs of compounds of Formula I and II include those where at least one of $R^1$ or $R^4$ is —$(CH_2)_{1-4}$Y, wherein Y is selected from the group consisting of —O—C(O)—$(CH_2)_n$—$CO_2H$; —O—C(O)—$(CH_2)_n$—$NH_2$; —O—P(O)(OR)$_2$; and —O—$SO_2R$, wherein R is —$(CH_2)_n$—$NH_2$ or —$(CH_2)_n$—$CO_2H$ and n is an integer from 1 to 10, preferably from 2 to 6. The free amino and carboxy groups can be converted to pharmaceutically acceptable salts or esters as described above. Prodrugs of the compounds of the present invention can be prepared according to conventional methods.

3',4'-di-O-camphanoyl-(+)-cis-khellactone analogs according to the present invention have been found to possess anti-retroviral, particularly anti-HIV, activity. The analogs of the present invention are expected to have improved water solubility, and enhanced oral bioavailability. Also, due to the improved water solubility, it will be easier to formulate the analogs of the present invention into pharmaceutical preparations. Further, 3',4'-di-O-camphanoyl-(+)-cis-khellactone analogs according to the present invention are expected to have improved biodistribution properties.

The invention is also directed to a method for treating a subject infected with HIV-1 by administering at least one of the above-noted 3',4'-di-O-camphanoyl-(+)-cis-khellactone analogs, optionally in combination with any one or more of the known anti-AIDS therapeutics or an immunostimulant.

Other features, advantages, embodiments, aspects and objects of the present invention will be clear to those skilled in the areas of relevant art, based upon the description, teaching and guidance presented herein.

The analogs of the present invention have been discovered to have anti-retroviral activity, thus providing suitable compounds and compositions for treating retroviral infections, optionally with additional pharmaceutically active ingredients, such as anti-retroviral, anti-HIV, and/or immuno-stimulating compounds or antiviral antibodies or fragments thereof.

By the term "anti-retroviral activity" or "anti-HIV activity" is intended suppression of viral replication whether by any of the following:

(1) viral pro-DNA integration into host cell genome;
(2) retroviral attachment to cells;
(3) viral entry into cells;
(4) cellular metabolism which permits viral replication;
(5) inhibition of intercellular spread of the virus;
(6) synthesis and/or cellular expression of viral antigens;
(7) activity of virus-coded enzymes (such as reverse transcriptase, integrase and proteases); and/or
(8) any known retroviral or HIV pathogenic actions, such as, for example, immunosuppression. Thus, any activity which tends to inhibit any of these mechanisms is "anti-retroviral activity" or "anti-HIV activity."

A 3',4'-di-O-camphanoyl-(+)-cis-khellactone analog of the present invention can be used for treatment of retroviral (e.g., HIV) infection either alone, or in combination with other modes of therapy known in the art. Such modes of therapy can include chemotherapy with drugs, such as, but not limited to, at least one of AZT, ddC, ddA, d4T, ddI, abacavir, nevirapine, delavirdine, efavirenz, saquinavir, ritonavir, indinavir, nelfinavir, amprenavir or any other anti-retroviral drugs or antibodies in combination with each other, or associated with a biologically based therapeutic, such as, for example, soluble CD4, antibodies to CD4, and conjugates of CD4 or anti-CD4, or as additionally presented herein.

Because some of the 3',4'-di-O-camphanoyl-(+)-cis-khellactone analogs of the present invention are relatively less or substantially non-toxic to normal cells, their utility is not limited to the treatment of established retroviral infections. For example, a 3',4'-di-O-camphanoyl-(+)-cis-khellactone analog according to the present invention can be used in treating blood products, such as those maintained in blood banks. The nation's blood supply is currently tested for antibodies to HIV. However, the test is still imperfect and samples which yield negative tests can still contain HIV virus. Treating the blood and blood products with the 3',4'-di-O-camphanoyl-(+)-cis-khellactone analogs of the present invention can add an extra margin of safety by killing any retrovirus that may have gone undetected.

In addition, 3',4'-di-O-camphanoyl-(+)-cis-khellactone analogs of the present invention can be used as prophylactics to prevent transmission of HIV infection between individuals. For example, the analogs can be administered orally or by injection to an HIV infected pregnant woman and/or fetus during pregnancy or immediately prior to, at, or subsequent to birth, to reduce the probability that the newborn infant becomes infected. Also, the analogs can be administered vaginally immediately prior to childbirth to prevent infection of the infant during passage through the birth canal. Further, the analogs of the present invention can be used during sexual intercourse to prevent transmission of HIV by applying a retroviral inhibiting effective amount of a topical composition including one or more compounds of Formula I or II to vaginal or other mucosa prior to sexual intercourse. For example, the analogs of the present invention can be used to prevent transmission of HIV from an infected male to an uninfected female or vice versa.

Pharmaceutical Compositions

Pharmaceutical compositions of the present invention can comprise at least one of the 3',4'-di-O-camphanoyl-(+)-cis-khellactone analogs. Pharmaceutical compositions according to the present invention can also further comprise other anti-viral agents such as, but not limited to, AZT (Glaxo Smith Kline), 3TC (Glaxo Smith Kline), ddI (Bristol-Myers Squibb), ddC (Hoffmann-La Roche), D4T (Bristol-Myers Squibb), abacavir (Glaxo Smith Kline), nevirapine (Boehringher Ingelheim), delavirdine (Pharmacia and Upjohn), efavirenz (DuPont Pharmaceuticals), saquinavir (Hoffmann-La Roche), ritonavir (Abbott Laboratories), indinavir (Merck and Company), nelfinavir (Agouron Pharmaceuticals), amprenavir (Glaxo Smith Kline), adefovir (Gilead Sciences) and hydroxyurea (Bristol-Myers Squibb).

Additional suitable antiviral agents for optimal use with a 3',4'-di-O-camphanoyl-(+)-cis-khellactone analog of the present invention can include, but are not limited to, AL-721 (lipid mixture) manufactured by Ethigen Corporation and Matrix Research Laboratories; Amphotericin B methyl ester; Ampligen (mismatched RNA) developed by DuPont/HEM Research; anti-AIDS antibody (Nisshon Food); 1 AS-101 (heavy metal based immunostimulant); Betaseron (β-interferon) manufactured by Triton Biosciences (Shell Oil); butylated hydroxytoluene; Carrosyn (polymannoacetate); Castanospermine; Contracan (stearic acid derivative); Creme Pharmatex (containing benzalkonium chloride) manufactured by Pharmalec; CS-87 (5-unsubstituted derivative of Zidovudine), Cytovene (ganciclovir) manufactured by Syntex Corporation; dextran sulfate; D-penicillamine (3-mercapto-D-valine) manufactured by Carter-Wallace and Degussa Pharmaceutical; Foscamet (trisodium phosphonoformate) manufactured by Astra AB; fusidic acid manufactured by Leo Lovens; glycyrrhizin (a constituent of licorice root); HPA-23 (ammonium-21-tungsto-9-antimonate) manufactured by Rhone-Poulenc Sante; human immune virus antiviral developed by Porton Products International; Ornidyl (eflornithine) manufactured by Merrell-Dow; nonoxinol; pentamidine isethionate (PENTAM-300) manufactured by Lypho Med; Peptide T (octapeptide sequence) manufactured by Peninsula Laboratories; Phenytoin (Warner-Lambert); Ribavirin; Rifabutin (ansamycin) manufactured by Adria Laboratories; CD4-IgG2 (Progenics Pharmaceuticals) or other CD4-containing or CD4-based molecules; T-20 (Trimeris) or other fusion inhibitors; Trimetrexate manufactured by Warner-Lambert Company; SK-818 (germanium-derived antiviral) manufactured by Sanwa Kagaku; suramin and analogues thereof manufactured by Miles Pharmaceuticals; UA001 manufactured by Ueno Fine Chemicals Industry; and Wellferon (α-interferon) manufactured by Glaxo Smith Kline.

Pharmaceutical compositions of the present invention can also further comprise immunomodulators. Suitable immunomodulators for optional use with a 3',4'-di-O-camphanoyl-(+)-cis-khellactone analog of the present invention in accordance with the present invention can include, but are not limited to: ABPP (Bropririmine); Ampligen (mismatched RNA) DuPont/HEM Research; anti-human interferon-α-antibody (Advance Biotherapy and Concepts); anti-AIDS antibody (Nisshon Food); AS-101 (heavy metal based immunostimulant); ascorbic acid and derivatives thereof; interferon-β; Carrosyn (polymannoacetate); Ciamexon (Boehringer-Mannheim); cyclosporin; cimetidine; CL-246,738 (American Cyanamid); colony stimulating factors, including GM-CSF (Sandoz, Genetics Institute); dinitrochlorobenzene; HE2000 (Hollis-Eden Pharmaceuticals); interferon-α; inteferon-gamma; glucan;

hyperimmune gamma-globulin (Bayer); IMREG-1 (leukocyte dialyzate) and IMREG-2 (IMREG Corp.); immuthiol (sodium diethylthiocarbamate) (Institut Merieux); interleukin-1 (Cetus Corporation; Hoffmann-LaRoche; Immunex); interleukin-2 (IL-2) (Chiron Corporation); isoprinosine (inosine pranobex); Krestin (Sankyo); LC-9018 (Yakult); lentinan (Ajinomoto/Yamanouchi); LF-1695 (Fournier); methionine-enkephalin (TNI Pharmaceuticals; Sigma Chemicals); Minophagen C; muramyl tripeptide, MTP-PE (Ciba-Geigy); naltrexone ("Trexan" DuPont); Neutropin, RNA immunomodulator (Nippon Shingaku); Remune (Immune Response Corporation); Reticulose (Advanced Viral Research Corporation); shosaikoto and ginseng; thymic humoral factor; TP-05 (Thymopentin, Ortho Pharmaceuticals); Thymosin factor 5 and Thymosin 1; Thymostimulin; TNF (Tumor necrosis factor) manufactured by Genentech; and vitamin B preparations.

The preferred animal subject of the present invention is a mammal. By the term "mammal" is meant an individual belonging to the class Mammalia. The invention is particularly useful in the treatment of human patients.

The term "treating" means the administering to subjects a 3',4'-di-O-camphanoyl-(+)-cis-khellactone compound for purposes which can include prevention, amelioration, or cure of a retroviral-related pathology.

Medicaments are considered to be provided "in combination" with one another if they are provided to the patient concurrently or if the time between the administration of each medicament is such as to permit an overlap of biological activity.

In one preferred embodiment, at least one 3',4'-di-O-camphanoyl-(+)-cis-khellactone compound comprises a single pharmaceutical composition.

Pharmaceutical compositions for administration according to the present invention can comprise at least one 3',4'-di-O-camphanoyl-(+)-cis-khellactone analog according to the present invention in a pharmaceutically acceptable form optionally combined with a pharmaceutically acceptable carrier. These compositions can be administered by any means that achieve their intended purposes. Amounts and regimens for the administration of a 3',4'-di-O-camphanoyl-(+)-cis-khellactone analog according to the present invention can be determined readily by those with ordinary skill in the clinical art of treating a retroviral pathology.

For example, administration can be by parenteral, such as subcutaneous, intravenous, intramuscular, intraperitoneal, transdermal, or buccal routes. Alternatively, or concurrently, administration can be by the oral route. The dosage administered depends upon the age, health and weight of the recipient, type of previous or concurrent treatment, if any, frequency of treatment, and the nature of the effect desired.

Compositions within the scope of this invention include all compositions comprising at least one 3',4'-di-O-camphanoyl-(+)-cis-khellactone analog according to the present invention in an amount effective to achieve its intended purpose. While individual needs vary, determination of optimal ranges of effective amounts of each component is within the skill of the art. Typical dosages comprise about 0.1 to about 100 mg/kg body weight. The preferred dosages comprise about 1 to about 100 mg/kg body weight of the active ingredient. The more preferred dosages comprise about 10 to about 100 mg/kg body weight. The most preferred dosages comprise about 10 to about 50 mg/kg body weight.

Therapeutic administration can also include prior, concurrent, subsequent or adjunctive administration of at least one additional 3',4'-di-O-camphanoyl-(+)-cis-khellactone analog according to the present invention or other therapeutic agent, such as an anti-viral or immune stimulating agent. In such an approach, the dosage of the second drug can be the same as or different from the dosage of the first therapeutic agent.

Administration of a compound of the present invention can also optionally include previous, concurrent, subsequent or adjunctive therapy using immune system boosters or immunomodulators. In addition to the pharmacologically active compounds, a pharmaceutical composition of the present invention can also contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 20 to 75 percent of active compound(s), together with the excipient.

Pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture, and processing the mixture of granules, after adding suitable auxiliaries, if desired or necessary, to obtain tablets or dragee cores.

Suitable excipients are, e.g., fillers such as saccharide, for example, lactose or sucrose, mannitol or sorbitol; cellulose preparations and/or calcium phosphates, such as tricalcium phosphate or calcium hydrogen phosphate; as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added such as the above-mentioned starches and also carboxymethyl starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions can be used, which can optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl cellulose phthalate are used. Dyestuffs or pigments can be added to the tablets or dragee coatings, for example, for identification or in order to characterize combinations of active compound doses.

Other pharmaceutical preparations which an be used orally include push-fit capsules made of gelatin, as well as soft, sealed capsules made of gelatin and a plasticizer such as glycerol or sorbitol. The push-fit capsules can contain the active compounds in the form of granules which can be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils or liquid paraffin. In addition, stabilizers can be added.

Possible pharmaceutical preparations which can be used rectally include, for example, suppositories which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions can be administered. Suitable lipophilic solvents or vehicles include fatty oils, such as sesame oil, or synthetic fatty acid esters, such as ethyl oleate or triglycerides. Aqueous injection suspensions that can contain substances which increase the viscosity of the suspension include, for example, sodium carboxymethyl cellulose, sorbitol, and/or dextran. Optionally, the suspension can also contain stabilizers.

A pharmaceutical formulation for systemic administration according to the invention can be formulated for enteral, parenteral or topical administration. Indeed, all three types of formulation can be used simultaneously to achieve systemic administration of the active ingredient.

Suitable formulations for oral administration include hard or soft gelatin capsules, dragees, pills, tablets, including coated tablets, elixirs, suspensions, syrups or inhalations and controlled release forms thereof.

Solid dosage forms in addition to those formulated for oral administration include rectal suppositories.

Prophylactic topical compositions for preventing HIV infection between individuals during childbirth or sexual intercourse include one or more compounds of Formula I or II and at least one pharmaceutically acceptable topical carrier or diluent. The topical composition can be, for example, in the form of an ointment, a cream, a gel, a lotion, a paste, a jelly, a spray, a foam, or a sponge. The dosage amount of a compound of Formula I or II in a prophylactic topical formulation is, in general, less than about 1,000 milligrams, preferably between about 0.01 to about 100 milligrams. The topical formulations can include other prophylactic ingredients. The carrier and diluents should be acceptable in the sense of being compatible with other ingredients of the formulation and not deleterious to the recipient.

Topical prophylactic formulations include those suitable for vaginal, rectal or topical administration. The formulations can, where appropriate, be conveniently presented in discrete dosage units, and can be prepared by any of the methods known in the art of pharmacy. All such methods include the step of bringing the active agent into association with liquid carriers, gels or finely divided solid carriers or both and then, if necessary, shaping the product into the desired formulation.

Prophylactic formulations suitable for vaginal administration can be presented as pessaries, tampons, creams, gels, pastes, jelly, foams, or sprays, or aqueous or oily suspensions, solutions or emulsions (liquid formulations) containing suitable carriers known in the art in addition to the active agent. Liquid formulations can contain conventional additives, such as, suspending agents, emulsifying agents, non-aqueous vehicles including edible oils, or preservatives. These formulations are useful to prevent both sexual transmission of HIV and infection of an infant during passage through the birth canal. In one example, the vaginal administration can take place prior to sexual intercourse, or immediately prior to childbirth.

Prophylactic formulations suitable for rectal or vaginal administration having a solid carrier are preferably represented as unit dose suppositories. Suitable carriers include cocoa butter and other materials commonly used in the art. Suppositories can be formed, for example, mixing one or more compounds of Formula I or II with one or more softened or melted carriers followed by chilling and shaping in molds.

Prophylactic formulations according to the invention can also be in the form of drops formulated with an aqueous or non-aqueous base comprising one or more dispersing agents, solubilizing agents, or suspending agents. Liquid sprays can be delivered from pressurized packs.

Prophylactic formulations according to the invention can be adapted to give sustained delivery. Also, the prophylactic formulations can include other active agents, such as spermicidal agents, antimicrobial agents, and anti-viral agents.

The 3',4'-di-O-camphanoyl-(+)-cis-khellactone analogs of the present invention can also be administered in the form of an implant when compounded with a biodegradable slow-release carrier. Alternatively, the 3',4'-di-O-camphanoyl-(+)-cis-khellactone analogs of the present invention can be formulated as a transdermal patch for continuous release of the active ingredient.

Suitable formulations for topical administration include creams, gels, jellies, mucilages, pastes and ointments. Suitable injectable solutions include intravenous subcutaneous and intramuscular injectable solutions. Alternatively, the 3',4'-di-O-camphanoyl-(+)-cis-khellactone analogs may be administered in the form of an infusion solution or as a nasal inhalation or spray.

The compounds of the present invention may be prepared using methods known to those skilled in the art. For example, compounds of Formula I where X and Z are both O, i.e., compounds of Formula II, can be prepared as illustrated by exemplary reactions in Schemes 1, 2 and 3. In Schemes 1 and 2, $R^2$ is hydrogen or $C_{1-4}$ alkyl. In Schemes 1, 2 and 3, R is (S)-camphanoyl. Accordingly, compounds of Formula II can be prepared by brominating 3- or 6-methyl substituted 3',4'-di-O-(S)-(−)-camphanoyl-(+)-cis-khellactone derivatives with N-bromosuccinimide at a molar ratio of 1:1 to anhydrous benzene to obtain corresponding bromomethyl derivatives (Chilin, A. et al., *J. Med. Chem.* 42:2936 (1999)). When excess N-bromosuccinimide is used, dibromomethyl derivatives are also obtained. The bromomethyl derivatives can be easily converted to other DCK analogs. The bromomethyl group on the coumarin nucleus can be acetylated with acetic anhydride in the presence of sodium acetate to afford acetoxymethyl derivatives. Subsequently, the acetate ester can be hydrolyzed in EtOH under acidic conditions to afford hydroxymethyl derivatives (Schade, B., et al., *J. Org. Chem.* 64:9109(1999)). Alternatively, bromomethyl derivatives can be reacted with hexamethylenetetramine followed by hydrolysis in the presence of a catalytic amount of HCl to give aminomethyl derivatives (Doucet, C., et al., *J. Med. Chem.* 42:4161 (1999)). To prepare dialkylamino derivatives, bromomethyl derivatives can be reacted with, for example, diethylamine in anhydrous toluene to give diethylamino derivatives (Chilin, A., et al., *J. Med. Chem.* 42:2936 (1999)). Each of these reactions are easy to perform at reflux temperatures.

SCHEME 1
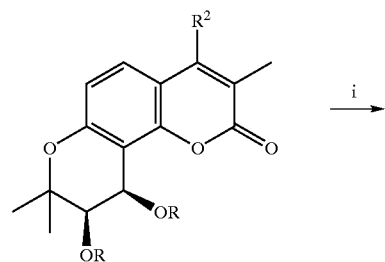
↓ i
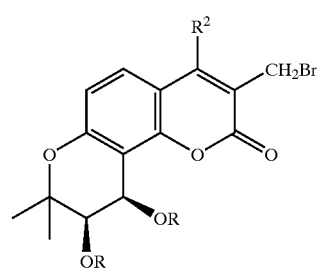
↓ ii
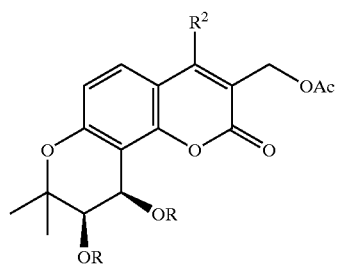
↓ iii
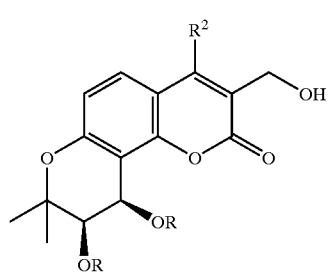
i. N-bromosuccinimide/benzene, reflux
ii. acetic anhydride/NaOAc, reflux
iii. EtOH/HCl, reflux
SCHEME 2
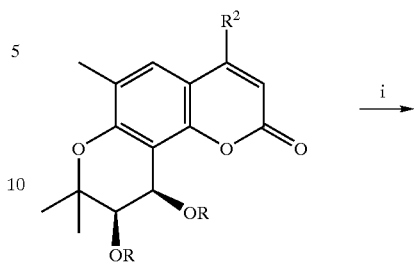
↓ i
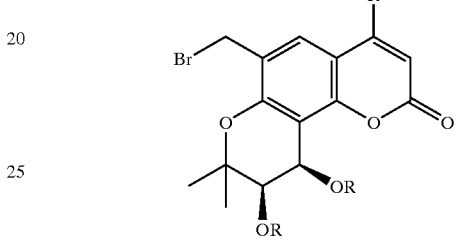
↓ ii
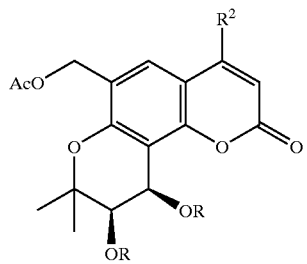
↓ iii
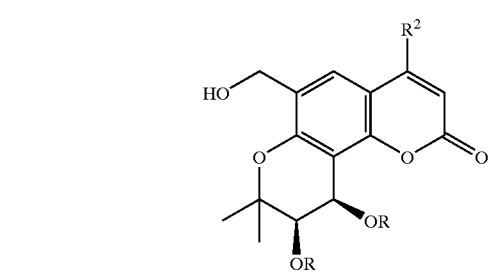
i. N-bromosuccinimide/benzene, reflux
ii. acetic anhydride/NaOAc, reflux
iii. EtOH/HCl, reflux

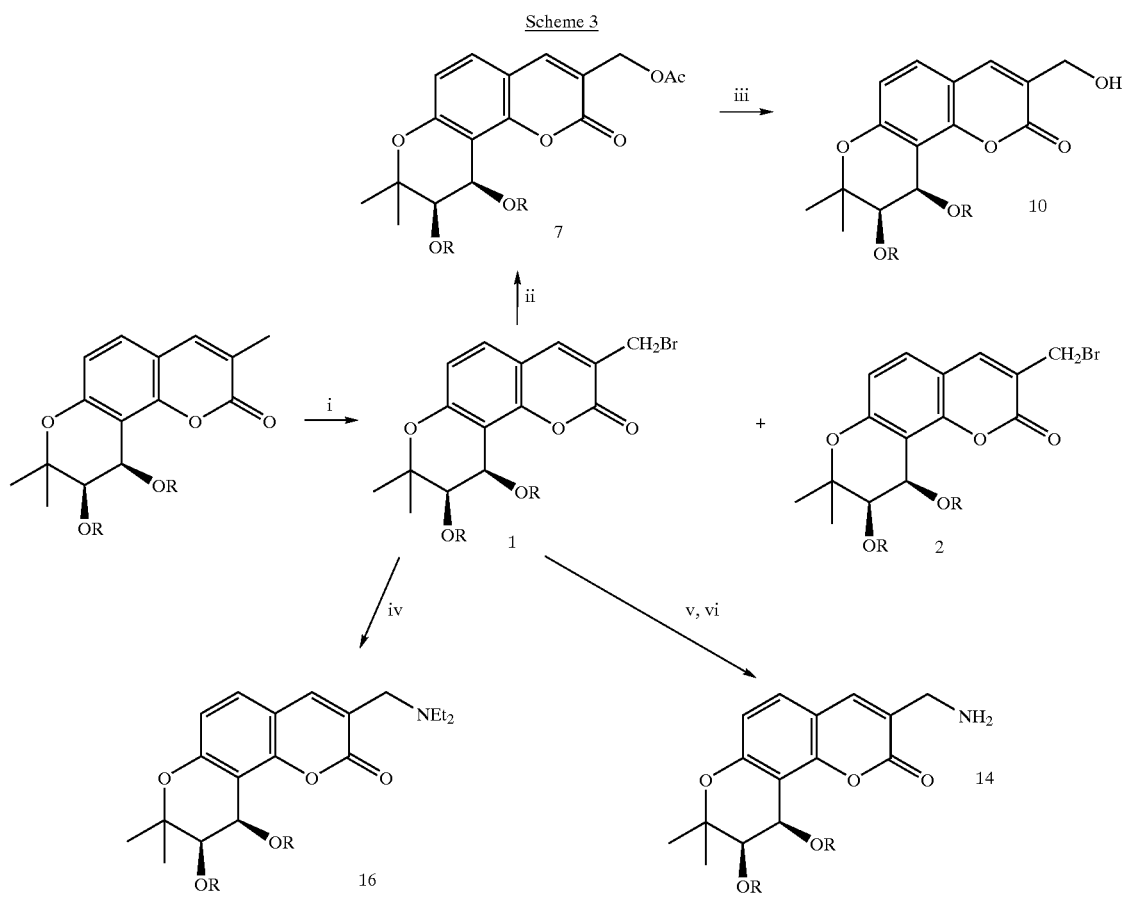

i. N-bromosuccinimide/benzene, reflux
ii. acetic anhydride/NaOAc, reflux
iii. EtOH/HCl, reflux
iv. diethylamine/toluene, reflux
v. hexamethylentetramine/CHCl$_3$
vi. EtOH/HCl, reflux The starting compounds in Schemes 1, 2 and 3 can be prepared, for example, as described by Xie, L., et al. (*J. Med. Chem.* 42:2662–2672 (1999) and *J. Med. Chem.* 44:664 (2001)). The starting materials for preparing compounds of Formula I can also be prepared by methods described in U.S. Pat. Nos. 5,847,165, 5,637,589, 5,726,204, and 5,612,341.

Compounds of Formula I where X is S can be prepared by methods analogous to those described above.

The starting compounds for preparing compounds of Formula I where X is NH can further be prepared, for example, as described by Yang, Z-Y, et al. (*Bioorg. Med. Chem. Lett.* 10:1003–1005 (2000)). Compounds of Formula I where X is NH can be prepared, for example, as described in Scheme 4:

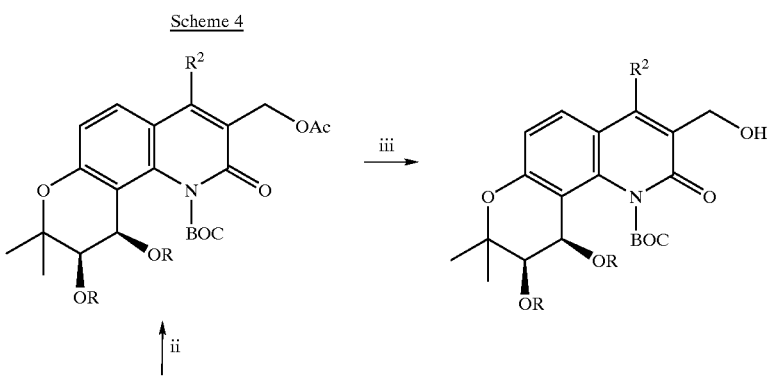

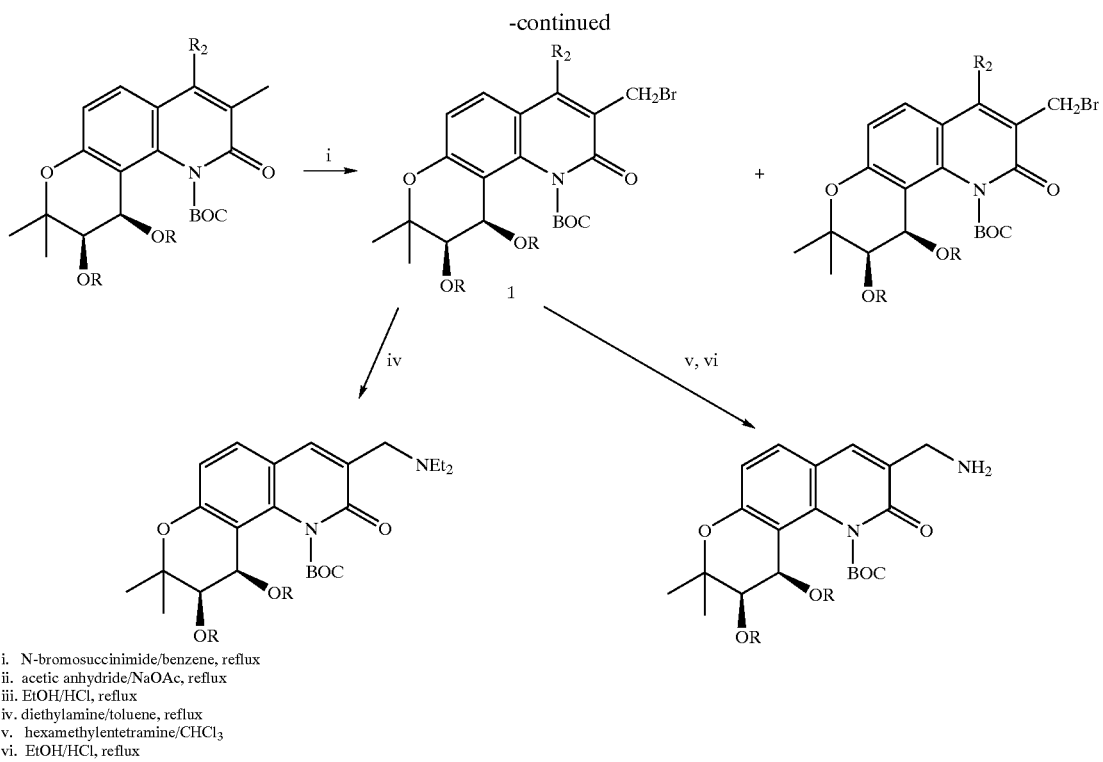

i. N-bromosuccinimide/benzene, reflux
ii. acetic anhydride/NaOAc, reflux
iii. EtOH/HCl, reflux
iv. diethylamine/toluene, reflux
v. hexamethylentetramine/CHCl$_3$
vi. EtOH/HCl, reflux The analogs of Scheme 4 can be deprotected with TFA to obtain the desired compounds of Formula I.

The biological evaluation of HIV-1 inhibition was carried out according to established protocols, (Kashiwada, Y., et al., *J. Med. Chem.* 39:1016–1017 (1996); Hashimoto, F., et al., *Bioorg. & Med. Chem.* 5:2133–2143 (1997)). The T cell line, H9, was maintained in continuous culture log-phase growth in complete medium (RPMI 1640 with 10% fetal calf serum supplemented with L-glutamine at 5% $CO_2$ and 37° C.). Test samples were first dissolved in dimethyl sulfoxide at a concentration of 10 mg/ml to generate master stocks with dilutions made into tissue culture media to generate working stocks. The following drug concentrations were used routinely for screening: 50, 5, and 0.5 µg/mL. For agents found to be active, additional dilutions were prepared for subsequent testing so that an accurate $EC_{50}$ value (defined below) could be determined. As the test samples were being prepared, an aliquot of the H9 cell line was infected with HIV-1 (IIIB isolate) while a second aliquot was mock-infected with complete medium. The virus stocks used for these studies typically had a $TCID_{50}$ value of 1×10$^6$/mL. An amount of virus equal to approximately 6.25×10$^4$ $TCID_{50}$ was added to the first aliquot of 3.5× 10$^6$H9 cells. The second aliquot received tissue culture medium only, and these mock-infected cells were used for toxicity determinations ($IC_{50}$ defined below). After a 4 h incubation at 37° C. and 5% $CO_2$, both cell populations were washed three times with fresh medium and then added to the appropriate wells of a 96-well plate containing various concentrations of the test drug or tissue culture medium (positive infected control/negative drug control). In addition, AZT was assayed during each experiment as a positive drug control. The plates were incubated at 37° C. and 5% $CO_2$ for 5 days. Cell-free culture supernatants were collected on Day 5 for use in a p24 antigen-capture ELISA assay to determine virus replication. p24 is the core protein of HIV and therefore is an indirect measure of the amount of virus present in the culture supernatants. Toxicity was determined using a viable dye method (XTT) on mock-infected H9 cells that were treated with test sample, AZT or no drug. If a test sample suppressed viral replication and was toxic to less than 50% of the cells, its effects were reported in the following terms: $IC_{50}$, the concentration of test sample which was toxic to 50% of the mock-infected H9 cells; $EC_{50}$, the concentration of the test sample which was able to suppress HIV replication by 50%; and Therapeutic Index (TI), the ratio of $IC_{50}$ to $EC_{50}$.

The following examples are illustrative, but not limiting, of the method, compounds and compositions of the present invention. Other suitable modifications and adaptations of the variety of conditions and parameters normally encountered and obvious to those skilled in the art are within the spirit and scope of the invention.

EXAMPLE 1

(3'R,4'R)-3',4'-Di-O-(S)-(−)-camphanoyl-3-hydroxymethyl-(+)-cis-khellactone
(3'R,4'R)-3',4'-Di-O-(S)-(−)-camphanoyl-3-methyl-(+)-cis-khellactone A mixture of $K_3Fe(CN)_6$ (150 mg, 0.75 mmol), $K_2CO_3$ (105 mg, 0.75 mmol), and 2,5-diphenyl-4,6-bis(9-O-dihydroquinyl)pyrimidine [(DHQ)$_2$-PYR] (4.4 mg, 0.005 mmol), $K_2OsO_2(OH)_4$ (0.005 mmol), was dissolved in 5 mL of t-BuOH/H$_2$O (v/v, 1:1) at room temperature. The solution was cooled to 0° C. and methanesulfonamide (0.23 mmol) added under stirring. When the solution turned from a light yellow to an orange color, 3-methylseselin (113 mg, 0.25 mmol) was added. The mixture was stirred at 0° C. for 2–4 days. Reaction was monitored using TLC, and at completion, $Na_2S_2O_5$ (excess), water, and CHCl$_3$ were added. After being stirred for half an hour at room temperature, the mixture was extracted with CHCl$_3$ three times. The combined organic layer was dried over $MgSO_4$, and then solvent was removed. The residue containing 3-methyl-(+)-cis-khellactone was directly acylated, without further purification, with (S)-(−)-camphanic chloride (greater than 0.5 mmol) in Py/CH$_2$Cl$_2$ for 1–2 days at room temperature. The mixture was diluted with EtOAc and washed with 10% aqueous HCl, water, and brine, successively. The organic phase was dired over anhydrous MgSO$_4$, filtered and concentrated. The residue was separated by TLC (eluant: hexane/EtOAc=7:3) to obtain the pure product. Yield 47%, white solid, mp 143–5° C. $^1$H NMR (CDCl$_3$): δ0.96–1.15 (15H, m.s., 5×CH$_3$), 1.45, 1.49 and 2.19 (each 3H, s, CH$_3$), 1.69, 1.92, 2.25, and 2.48 (each 2H, m, CH$_2$ in camphanoyl group), 2.16 (3H, s, CH$_3$-3), 5.40 (1H, d, J=4.8 Hz, H-3'), 6.66 (1H, d, J=4.8 Hz, H-4'), 6.80 (1H, d, J=8.8 Hz, H-6), 7.35 (1H, d, J=8.8 Hz, H-5) and 7.43 (1H, s, H-4).

The following compounds were prepared similarly:

(3'R,4'R)-3',4'-Di-O-(S)-(−)-camphanoyl-3,4-dimethyl-(+)-cis-khellactone; yield 64%; white solid, mp 118–20° C.; $^1$H NMR (CDCl$_3$): δ0.93-1.12 (15H, m.s., 5×CH$_3$) 1.27, 1.49, and 1.55 (each 3H, s, CH$_3$), 1.73, 1.92, 2.20, and 2.48 (each 2H, m, CH$_2$ in camphanoyl group), 2.13 (3H, s, CH$_3$-3), 2.38 (3H, s, CH$_3$-4), 5.40 (1H, d, J=4.8 Hz, H-3'), 6.66 (1H, d, J=4.8 Hz, H-4'), 6.63 (1H, d, J=8.8 Hz, H-6), and 7.54 (1H, d, J=8.8 Hz, H-5).

(3'R,4'R)-3',4'-Di-O-(S)-(−)-camphanoyl-6-methyl-(+)-cis-khellactone; yield 28%; white solid, mp 206–7° C.; $^1$H NMR (CDCl$_3$): δ0.92–1.12 (15H, m.s., 5×CH$_3$), 1.47, 1.49, and 2.05 (each 3H, s, CH$_3$), 1.66, 1.92, 2.23, and 2.48 (each 2H, m, CH$_2$ in camphanoyl group), 2.23 (3H, s, CH$_3$-6), 5.39 (1H, d, J=4.8 Hz, H-3'), 6.22 (1H, d, J=9.8 Hz, H-3), 6.66 (1H, d, J=4.8 Hz, H-4'), 7.26 (1H, s, H-5), and 7.58 (1H, d, J=9.8 Hz, H-4).

(3'R,4'R)-3',4'-Di-O-(S)-(−)-camphanoyl-4,6-dimethyl-(+)-cis-khellactone; yield 68%; white solid, mp 250° C. (dec.); $^1$H NMR (CDCl$_3$): δ0.99–1.11 (18H, m.s., 6×CH$_3$), 1.47, and 1.49 (each 3H, s, CH$_3$), 1.65, 1.92, 2.20, and 2.45 (each 2H, m, CH$_2$ in camphanoyl group), 2.25 (3H, s, CH$_2$-6), 2.98 (3H, s, CH$_3$-4), 5.39 (1H, d, J=4.8 Hz, H-3'), 6.09 (1H, s, H-3), 6.65 (1H, d, J=4.8 Hz, H-4'), and 7.37 (1H, s, H-5).

(3'R,4'R)-3',4'-Di-O-(S)-(−)-camphanoyl-3-bromomethyl-(+)-cis-khellactone (1)

A mixture of (3'R,4'R)-3',4'-di-O-(S)-(−)-camphanoyl-3-methyl-(+)-cis-khellactone and N-bromosuccinimide at a molar ratio of 1:1 in anhydrous benzene was refluxed until (3'R,4'R)-3',4'-di-O-(S)-(−)-camphanoyl-3-methyl-(+)-cis-khellactone had disappeared. The solvent was evaporated under reduced pressure. The residue was purified by column chromatography to afford (3'R,4'R)-3',4'-di-O-(S)-(−)-camphanoyl-3-bromomethyl-(+)-cis-khellactone.

Yield 77%. $^1$H NMR (CDCl$_3$): δ0.98–1.11 (18H, m.s., 6×CH$_3$), 1.45, and 1.49 (each 3H, s, CH$_3$), 1.68, 1.91, 2.24, and 2.51 (each 2H, m, CH$_2$ in camphanoyl group), 4.38 (2H, s, CH$_2$-4), 5.39 (1H, d, J=4.8 Hz, H-3'), 6.64 (1H, d, J=4.48 Hz, H-4'), 6.48 (1H, d, J=8.7 Hz, H-6), 7.42 (1H, d, J=8.7 Hz, H-5), and 7.76 (1H, s, H-4).

The following compounds were prepared similarly:

(3'R,4'R)-3',4'-Di-O-(S)-(−)-camphanoyl-3-dibromomethyl-(+)-cis-khellactone (2)(with excess N-bromosuccinimide); $^1$H NMR (CDCl$_3$): δ0.98–1.11 (18H, m.s., 6×CH$_3$), 1.46 and 1.50 (each 3H, s, CH$_3$), 1.63, 1.89, 2.23, and 2.48 (each 2H, m, CH$_2$ in camphanoyl group), 5.39 (1H, d, J=4.8 Hz, H-3'), 6.64 (1H, d, J=4.8 Hz, H-4'), 6.74 (1H, s, CH-4), 6.89 (1H, d, J=8.7 Hz, H-6), 7.54 (1H, d, J=8.7 Hz, H-5), and 8.24 (1H, s, H-4).

(3'R,4'R)-3',4'-Di-O-(S)-(−)-camphanoyl-3-bromomethyl-4-methyl-(+)-cis-khellactone (3); yield 86%; $^1$H NMR (CDCl$_3$): δ0.97–1.11 (18H, m.s., 6×CH$_3$), 1.44 and 1.48 (each 3H, s, CH$_3$), 1.68, 1.93, 2.22, and 2.51 (each 2H, m, CH$_2$ in camphanoyl group), 2.42 (3H, s, CH$_3$-4), 4.51 (2H, s, CH$_2$-3), 5.38 (1H, d, J=4.8 Hz, H-3'), 6.63 (1H, d, J=4.8 Hz, H-4'), 6.86 (1H, d, J=8.7 Hz, H-6), 7.60 (1H, d, J=8.7 Hz, H-5).

(3'R,4'R)-3',4'-Di-O-(S)-(−)-camphanoyl-6-bromomethyl-(+)-cis-khellactone (4); $^1$H NMR (CDCl$_3$): δ0.98–1.11 (18H, m.s., 6×CH$_3$), 1.45, and 1.49 (each 3H, s, CH$_3$), 1.68,1.91, 2.24, and 2.51 (each 2H, m, CH$_2$ in camphanoyl group), 4.52 and 4.55 (each 1H, d, J=7.0 Hz, CH$_2$-6), 5.44 (1H, d, J=4.8 Hz, H-3'), 6.27 (1H, d, J=8.7 Hz, H-3), 6.66 (1H, d, J=4.8 Hz, H-4'), 7.50 (1H, s, H-5), and 7.60 (1H, d, J=8.7 Hz, H-4).

(3'R,4'R)-3',4'-Di-O-(S)-(−)-camphanoyl-6-dibromomethyl-4-methyl-(+)-cis-khellactone (5) (with excess N-bromosuccinimide); $^1$H NMR (CDCl$_3$): δ0.98-1.13 (18H, m.s., 6×CH$_3$), 1.26, and 1.54 (each 3H, s, CH$_3$), 1.62, 1.91, 2.20, and 2.51 (each 2H, m, CH$_2$ in camphanoyl group), 2.48 (3H, s, CH$_3$-4), 5.43 (1H, d, J=4.8 Hz, H-3'), 6.18 (1H, s, H-3), 6.64 (1H, d, J=4.8 Hz, H-4'), 7.01 (1H, s, CH-6), and 8.09 (1H, s, H-5).

(3'R,4'R)-3',4'-Di-O-(S)-(−)-camphanoyl-6-bromomethyl-4-methyl-(+)-cis-khellactone (6); yield 67%; $^1$H NMR (CDCl$_3$): δ0.98–1.11 (18H, m.s., 6×CH$_3$), 1.52 and 1.53 (each 3H, s, CH$_3$), 1.70, 1.90, 2.20, and 2.51 (each 2H, m, CH$_2$ in camphanoyl group), 2.40 (3H, s, CH$_3$-4), 4.53 and 4.56 (each 1H, d, J=7.0 Hz, CH$_2$-6), 5.43 (1H, d, J=4.8 Hz, H-3), 6.13 (1H, s, H-3), 6.65 (1H, d, J=4.8 Hz, H-4'), and 7.59 (1H, s, H-5).

(3'R,4'R)-3',4'-Di-O-(S)-(−)-camphanoyl-3-acetoxymethyl-(+)-cis-khellactone (7)

A mixture of (3'R,4'R)-3',4'-di-O-(S)-(−)-camphanoyl-3-bromomethyl-(+)-cis-khellactone and anhydrous sodium acetate (excess) in acetic anhydride was refluxed until the starting material disappeared. The mixture was cautiously poured into ice-water and allowed to stand overnight. The precipitate was filtered, then washed with water until neutral to give pure (3'R,4'R)-3',4'-di-O-(S)-(−)-camphanoyl-3-acetoxymethyl-(+)-cis-khellactone. Yield 79%. $^1$H NMR (CDCl$_3$): δ0.95–1.11 (18H, m.s., 6×CH$_3$), 1.46 and 1.49 (each 3H, s, CH$_3$), 1.62, 1.90, 2.24, and 2.49 (each 2H, m, CH$_2$ in camphanoyl group), 2.19 (3H, s, COCH$_3$), 5.00 (2H, m, CH$_2$-3), 5.40 (1H, d, J=4.8 Hz, H-3'), 6.64 (1H, d, J=4.8 Hz, H-4'), 6.83 (1H, d, J=8.7 Hz, H-6), 7.42 (1H, d, J=8.7 Hz, H-5), and 7.69 (1H, s, H-4).

The following compounds were prepared similarly:

(3'R,4'R)-3',4'-Di-O-(S)-(−)-camphanoyl-3-acetoxymethyl-4-methyl-(+)-cis-khellactone (8); yield 86%; $^1$H NMR (CDCl$_3$): δ0.95–1.11 (18H, m.s., 6×CH$_3$), 1.44 and 1.48 (each 3H, s, CH$_3$), 1.62, 1.90, 2.24, and 2.49 (each 2H, m, CH$_2$ in camphanoyl group), 2.05 (3H, s, COCH$_3$), 2.48 (3H, s, CH$_3$-4), 5.13 (2H, s, CH$_2$-3), 5.39 (1H, d, J=4.8 Hz, H-3'), 6.63 (1H, d, J=4.8 Hz, H-4'), 6.85 (1H, d, J=8.7 Hz, H-6), and 7.61 (1H, d, J=8.7 Hz, H-5).

(3'R,4'R)-3',4'-Di-O-(S)-(−)-camphanoyl-6-acetoxymethyl-4-methyl-(+)-cis-khellactone (9); yield 84%; $^1$H NMR (CDCl$_3$): δ0.92–1.11 (18H, m.s., 6×CH$_3$), 1.47 and 1.49 (each 3H, s, CH$_3$), 1.62, 1.90, 2.22, and 2.46 (each 2H, m, CH$_2$ in camphanoyl group), 2.12 (3H, s, COCH$_3$), 2.41 (3H, s, CH$_3$-4), 5.18 (2H, s, CH$_2$-6), 5.39 (1H, d, J=4.8 Hz, H-3'), 6.12 (1H, s, H-3), 6.63 (1H, d, J=4.8 Hz, H-4'), and 7.60 (1H, s, H-5).

(3'R,4'R)-3',4'-Di-O-(S)-(−)-camphanoyl-3-hydroxymethyl-(+)-cis-khellactone (10)

(3'R,4'R)-3',4'-Di-O-(S)-(−)-camphanoyl-3-acetoxymethyl-(+)-cis-khellactone in EtOH in the presence of catalytic amount of HCl (2N) was refluxed for 1–2 hours. The mixture was poured into ice-water and allowed to stand overnight. The solid was collected and washed with water three times until neutral. The resulting (3'R,4'R)-3',4'-di-O-(S)-(−)-camphanoyl-3-hydroxymethyl-(+)-cis-khellactone was purified by preparative TLC. Yield 79%. $^1$H NMR (CDCl$_3$): δ0.98–1.11 (18H, m.s., 6×CH$_3$), 1.45 and 1.49 (each 3H, s, CH$_3$), 1.62, 1.90, 2.22, and 2.49 (each 2H, m, CH$_2$ in camphanoyl group), 4.56 (2H, m, CH$_2$-3), 5.39 (1H, d, J=4.8 Hz, H3'), 6.65 (1H, d, J=4.8 Hz, H-4'), 6.83 (1H, d, J=8.7 Hz, H-6), 7.43 (1H, d, J=8.7 Hz, H-5), and 7.67 (1H, s, H-4).

The following compounds were prepared similarly:

(3'R,4'R)-3',4'-Di-O-(S)-(−)-camphanoyl-3-hydroxymethyl-4-methyl-(+)-cis-khellactone (11); yield 85%; $^1$H NMR (CDCl$_3$): δ0.90–1.11 (18H, m.s., 6×CH$_3$), 1.45 and 1.49 (each 3H, s, CH$_3$), 1.62, 1.90, 2.24, and 2.46 (each 2H, m, CH$_2$ in camphanoyl group), 2.47 (3H, s, CH$_3$-4), 4.66 (2H, s, CH$_2$-3), 5.40 (1H, d, J=4.8 Hz, H-3'), 6.66 (1H, d, J=4.8 Hz, H-4'), 6.87 (1H, d, J=8.7 Hz, H-6), and 7.61 (1H, d, J=8.7 Hz, H-5).

(3'R,4'R)-3',4'-Di-O-(S)-(−)-camphanoyl-6-hydroxymethyl-4-methyl-(+)-cis-khellactone (12); yield 87%; $^1$H NMR (CDCl$_3$): δ0.92–1.11 (18H, m.s., 6×CH$_3$), 1.48 and 1.51 (each 3H, s, CH$_3$), 1.62, 1.90, 2.22, and 2.49 (each 2H, m, CH$_2$ in camphanoyl group), 2.41 (3H, s, CH$_3$-4), 4.74 (2H, s, CH$_2$-6), 5.41 (1H, d, J=4.8 Hz, H-3'), 6.13 (1H, s, H-3), 6.66 (1H, d, J=4.8 Hz, H-4'), and 7.63 (1H, s, H-5).

EXAMPLE 2

(3'R,4'R)-3',4'-Di-O-(S)-(−)-camphanoyl-6-(dimethylphosphate)methyl-4-methyl-(+)-cis-khellactone (13)

A mixture of (3'R,4'R)-3',4'-di-O-(S)-(−)-camphanoyl-6-bromomethyl-4-methyl-(+)-cis-khellactone and dimethyl phosphate at a molar ratio of 1:6 in acetonitrile was heated to 70° C. in the presence of excess CsF for 8 h. After the solvent was removed under reduced pressure, the residue was separated by preparative TLC to give pure product 13 in a 75% yield. $^1$H NMR (CDCl$_3$): δ0.98–1.11 (18H, m.s., 6×CH$_3$), 1.48 and 1.50 (each 3H, s, CH$_3$), 1.62, 1.90, 2.20, and 2.50 (each 2H, m, CH$_2$ in camphanoyl group), 2.41 (3H, s, CH$_3$-4), 3.79 and 3.82 (each 3H, s, POCH$_3$), 5.13 (2H, m, CH$_2$-6), 5.40 (1H, d, J=4.8 Hz, H-3'), 6.19 (1H, s, H-3), 6.65 (1H, d, J=4.8 Hz, H-4'), and 7.68 (1H, s, H-5).

EXAMPLE 3

(3'R,4'R)-3',4'-Di-O-(S)-(−)-camphanoyl-3-aminomethyl-(+)-cis-khellactone (14)

(3'R,4'R)-3',4'-Di-O-(S)-(−)-camphanoyl-3-methyl-(+)-cis-khellactone and hexamethyltetraamine at a molar ratio of 1:1:5 in CHCl$_3$ was relaxed for 3 hours. After removal of solvent in vaccine, the residue was heated in EtOH in the presence of catalytic amount of HCl (2N) at 100° C. for about 30 minutes. After cooling, the precipitate was filtered and discarded, and the solvent was removed under reduced pressure. The pure (3'R,4'R)-3',4'-di-O-(S)-(−)-camphanoyl-3-aminomethyl-(+)-cis-khellactone was obtained by preparative TLC. Yield 76%. $^1$H NMR (CDCl$_3$): δ0.98–1.11 (18H, m.s., 6×CH$_3$), 1.45 and 1.49 (each 3H, s, CH$_3$), 1.69, 1.90, 2.23, and 2.50 (each 2H, m, CH$_2$ in camphanoyl group), 2.60 (s, br., NH$_2$), 3.79 (2H, s, CH$_2$-3), 5.39 (1H, d, J=4.8 Hz, H-3'), 6.65 (1 H, d, J=4.8 Hz, H-4'), 6.82 (1H, d, J=8.7 Hz, H-6), 7.42 (1H, d, J=8.7 Hz, H-5), and 7.67 (1H, s, H-4).

Similarly was prepared (3'R,4'R)-3',4'-di-O-(S)-(−)-camphanoyl-6-aminomethyl-4-methyl-(+)-cis-khellactone (15); yield 57%; $^1$H NMR (CDCl$_3$): δ0.98–1.11 (18H, m.s., 6×CH$_3$), 1.48 and 1.51 (each 3H, s, CH$_3$), 1.62, 1.90, 2.22, and 2.49 (each 2H, m, CH$_2$ in camphanoyl group), 2.41 (3H, s, CH$_3$-4), 3.88 (2H, s, CH$_2$-6), 5.41 (1H, d, J=4.8 Hz, H-3'), 6.11 (1H, s, H-3), 6.66 (1H, d, J=4.8 Hz, H-4'), and 7.55 (1H, s, H-5).

EXAMPLE 4

(3'R,4'R)-3',4'-Di-O-(S)-(−)-camphanoyl-3-diethylaminomethyl-(+)-cis-khellactone (16)

A mixture of (3'R,4'R)-3',4'-di-O-(S)-(−)-camphanoyl-3-bromomethyl-(+)-cis-khellactone and excess diethylamine in anhydrous toluene was refluxed for 6 h. After removal of solvent, the residue was separated by TLC to get pure product 16 in a 71% yield. $^1$H NMR (CDCl$_3$): δ0.98–1.11 (18H, m.s., 6×CH$_3$), 1.07 (6H, t, J=7.0 Hz, 2×CH$_3$), 1.45 and 1.49 (each 3H, s, CH$_3$) 1.69, 1.90, 2.22 and 2.50 (each 2H, m, CH$_2$ in camphanoyl group), 2.60 (4H, f, J=7.0 Hz, 2×NCH$_2$), 3.47 (2H, s, CH$_2$-3), 5.39 (1H, d, J=4.8 Hz, H-3'), 6.65 (1 H, d, J=4.8 Hz, H-4'), 6.81 (1H, d, J=8.7 Hz, H-6), 7.43 (1H, d, J=8.7 Hz, H-5), and 7.81 (1H, s, H-4).

EXAMPLE 5

Pharmacological Activity

Compounds of the present invention were assayed for anti-HIV activity according to the following assay procedures. The T cell line, H9, and the promonocytic cell line, U937, were maintained separately in continuous culture with complete medium (RPMI 1640 with 10% fetal calf serum) at 5% CO$_2$ and 37° C. The cell lines were used in experiments only when in the logarithmic phase of growth, whereas uninfected peripheral blood mononuclear cells (PBMCs) were first stimulated with PHA (1 μg/mL) for three days. All cell targets were incubated with HIV-1 (IIIB isolate, 1×10$^6$ TCID$_{50}$/mL) for one hour at 37° C. and 5% CO$_2$. The cell lines and PBMCs were washed thoroughly to remove unadsorbed virions and resuspended at 4×10$^5$ cells/mL in complete medium or complete medium with 10% v/v interleukin 2 (IL-2), respectively. 100 mL aliquots were placed into wells of 96-well tissue culture plates containing an equal volume of test compounds (diluted in the appropriate culture medium). The toxicity of each compound was assessed by determining the viability of compound-exposed uninfected cells after five days at 37° C. and 5% CO$_2$. A p24 antigen ELISA assay was used to determine the level of virus released in the medium of the HIV-infected cultures. The p24 antigen assay used a HIV-1 anti-p24 specific monoclonal antibody as the capture antibody coated onto 96-well plates. Following a sample incubation period, rabbit serum containing antibodies for HIV-1 p24 was used to tag any p24 captured onto the microtiter well surface. Peroxidase conjugated goat anti-rabbit serum was then used to tag HIV-1 p24 specific rabbit antibodies that had complexed with captured p24. The presence of p24 in test samples was then revealed by addition of substrate. p24 in the culture medium was quantitated against a standard curve containing known amounts of p24. The effective (EC$_{50}$) and inhibitory (IC$_{50}$) concentrations for anti-HIV activity and cytotoxicity, respectively, were determined.

TABLE 1

Anti-HIV Activities of Compounds 1–16 and AZT.

| Compound | Anti-HIV* Activity EC$_{50}$ (µg/mL) | Cytotoxicity* IC$_{50}$ (µg/mL) | Therapeutic* Index (TI = IC$_{50}$/EC$_{50}$) |
|---|---|---|---|
| 1  | 8.54 × 10$^{-2}$ | 3.38  | 40      |
| 2  | 1.19 × 10$^{-4}$ | 3.20  | 26,890  |
| 3  | 1.92 × 10$^{-4}$ | 19.4  | 101,000 |
| 4  | 1.76 × 10$^{-2}$ | 1.99  | 113     |
| 5  | 2.15 × 10$^{-2}$ | 1.76  | 81.8    |
| 6  | 2.5 × 10$^{-2}$  | 25.00 | 1,000   |
| 7  | 1.03 × 10$^{-3}$ | 3.34  | 3,243   |
| 8  | 1.20 × 10$^{-4}$ | 18.80 | 157,000 |
| 9  | 0.275            | 21.70 | 78.9    |
| 10 | 1.88 × 10$^{-4}$ | 35.35 | 188,032 |
| 11 | 1.61 × 10$^{-2}$ | 21.2  | 1,320   |
| 12 | 6.25 × 10$^{-4}$ | 19.3  | 30,900  |
| 13 | 0.504            | 1.91  | 3.79    |
| 14 | 0.39             | 32.81 | 208     |
| 15 | 1.00 × 10$^{-3}$ | 24.1  | 24,100  |
| 16 | 0.69             | 43.01 | 62      |
| AZT| 0.045            | 1875  | 41,667  |

*all the data represented as average of at least two experiments.

Compounds 1–16 and AZT were examined for anti-HIV activity in H-9 lymphocytes as shown in Table 1. All the tested compounds have anti-viral activity, compounds 2, 3, 7, 8, 10, 12, and 15 being the most potent ones.

EXAMPLE 6

Disposition of Compound 11 and 4-Methyl-DCK in Rats

Studies of the disposition of compound 11 ((3'R,4'R)-3',4'-di-O-(S)-(−)-camphanoyl-3-hydroxymethyl-4-methyl-(+)-cis-khellactone) and 4-methyl-DCK ((3'R,4'R)-3',4'-di-O-(S)-(−)-camphanoyl-4-methyl-(+)-cis-khellactone) were conducted in rats. 4-Methyl-DCK can be prepared, for example, as described in U.S. Pat. No. 5,847,165. The rats ordered from Charles River with jugular catheters in place were allowed to acclimate for one to two days prior to use. The venous catheter was kept patent by flushing daily with heparin solution.

Assay of the Disposition of Compound 11 in Rats

Weighed amount of compound 11 was suspended in 0.5% hydroxypropyl cellulose, then administered to three rats by oral gavage using a feeding needle to provide oral doses of 27.3, 26.7, and 19.3 mg/kg. Blood samples (0.4 mL) were collected at 0, 0.25, 0.50, 0.75, 1.0, 1.5, 2, 4, and 8 hours following the oral dosing. The samples were centrifuged and 0.10 mL of plasma was aliquoted into two tubes. The plasma samples were frozen at −20° C. prior to analysis. The samples were thawed and analyzed by reversed phase HPLC within two weeks of collection.

Five rats were also dosed by the intravenous route with a dissolution of compound 11 in DMSO and absolute ethanol (1:1.5). The volume injected to the tail vein was limited to 0.25 mL or less. After adjusting for body weight of of animals, the three doses were 10.7, 10.6, 10.6, 8.77, and 5.66 mg/kg. Blood collection of 0.4 mL collected sequentially over eight hours provided plasma samples obtained as described above.

Reversed phase HPLC was conducted with an ODS, 5 µM particle size, 150×10 mm Axxiom column (Thompson Instruments, Chantilly, Va.) using 55% acetonitrile and water as the mobile phase with 25 mM acetic acid buffer at 1.5 mL/min. Detection was carried out at 320 nm ($\lambda_{max}$) for UV detection and at an excitation wavelength of 320 nm. The equipment for HPLC was an HP 1100 system with UV and quantitative analysis was performed using the HP Chemstation.

The HPLC assay was partially validated with a detection limit of 0.05 µg/mL. Standard curves were prepared by the addition of appropriate diluted stock solutions of compound 11 to 0.10 mL plasma (pooled human plasma) to provide concentration of zero, and 0.01 to 20 µg/mL in a 1.5 mL microcentrifuge tube. Three volumes (0.3 mL) of acetonitrile were then added to each tube with vortexing, followed by cooling on ice for 10 minutes to precipitate proteins. Following centrifugation (12,000 rpm for 5 minutes), the supernatant was decanted to another 1.5 mL microcentrifuge tube. External standard solution (0.025 mL of 0.0 1 mg/mL of DCK) was added to each tube. The supernatant was then evaporated to dryness with a stream of nitrogen at room temperature. The residue was reconstituted with 0.15 mL mobile phase with vortexing. Aliquots of 75 µL of the solution were then injected onto the HPLC column. The retention time of compound 11 was approximately 6.0 minutes and the retention time for DCK was 9.6 minutes. Recovery from plasma was determined by spiking compound 11 into plasma the same way as was done in the preparation of the standard curve, and preparing samples as described above.

Assay of the Disposition of 4-methyl-DCK in Rats

Weighed amounts (approximately 7–8 mg) of 4-methyl-DCK were suspended in 1 mL of 10% Tween 80/water, then administered to two rats (250–300 g) by oral gavage using a feeding needle to provide an oral dose of 25 mg/kg. Blood samples (0.3 mL) were collected at 0, 0.25, 0.50, 0.75, 1.0, 1.5, 2, 4, 8, and 23 hours following the oral dosing. Approximately 0.01 mL of heparin was added to each sample. The samples were then centrifuged to collect 0.10 mL of plasma. The plasma samples were frozen at −20° C. prior to analysis. The samples were thawed and analyzed by reversed phase HPLC within two weeks of collection.

Reversed phase HPLC was conducted with an ODS, 5 µM particle size, 150×10 mm Axxiom column (Thompson Instruments, Chantilly, Va.) using 60% acetonitrile/0.1% TFA in water as the mobile phase. Detection was carried out at 320 nm ($\lambda_{max}$) for UV detection. The equipment for HPLC was an HP 1050 quaternary HPLC pump, an HP 1050 UV detector at 320 nm and range 0.2, an HP 3390 integrator, and a BioRad Model AS-100 autosampler.

Standard curves were prepared by addition of appropriate diluted stock solutions of 4-methyl-DCK to 0.10 mL plasma (pooled human plasma) to provide concentration of zero, and 0.05 to 20 µg/mL in a 13×100 mm culture tube. Internal standard solution (0.025 mL of 0.01 mg/mL DCK) was then added to each tube. The spiked samples were briefly vortexes, then allowed to equilibrate for at least 10 minutes prior to further workup. Three volumes (0.3 mL) of acetonitrile was then added to each tube with vortexing for one minute, followed by cooling on ice for 10 minutes to precipitate proteins. Following centrifugation (approximately 3000×g), the supernatant was decanted to another 13×100 mm culture tube and evaporated to dryness with a stream of nitrogen at room temperature. The residue was reconstituted with 0.20–0.50 mL mobile phase with sonication for 3 seconds and vortexing for one minute. Finally, approximately half of the final volume, 0.1 to 0.2 mL of solution, was injected onto the HPLC column. The retention times for DCK and 4-methyl-DCK were approximately 6–7 and 8–9 minutes, respectively.

The HPLC assay was partially validated to have a range of 0.125 to 20 µg/mL in plasma, with a detection limit of 50 ng/mL. Recovery from plasma was determined by spiking 4-methyl-DCK into plasma the same way as was done in the preparation of the standard curve, and preparing samples as described above, but adding DCK as an external standard just prior to injection. These samples were compared to unextracted samples in buffer, also prepared with DCK added just prior injection to serve as an external standard. Peak ratio of 4-methyl-DCK/DCK were then compared to estimate extraction efficiency of the direct precipitation method. Intraday variability was done by preparing replicate (n=5) samples of 4-methyl-DCK in plasma at five concentrations employed for the standard curve that included the three lowest concentrations of 0.05, 0.125, and 0.25 μg/mL.

Results

Detectable concentrations of compound 11 were seen in plasma after oral administration with $C_{max}$ of 0.235 μg/mL occurring around 120–240 minutes. The clearance of compound 11 after intravenous administration was 83 mL/min/kg. The results show that the oral bioavailability ($F_{oral}$) of compound 11 is 15% estimated from mean oral and intravenous administration data. No detectable concentrations were seen in plasma after oral administration of 25 mg/kg of 4-methyl-DCK, i.e., the concentration in plasma was less than 50 ng/mL and, thus, the bioavailability ($F_{oral}$) of 4-methyl-DCK could not be determined.

Those skilled in the art will recognize that while specific embodiments have been illustrated and described, various modifications and changes may be made without departing from the spirit and scope of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. All publications, patent applications and patents cited herein are fully incorporated by reference.

What is claimed is:

1. A compound of Formula I:

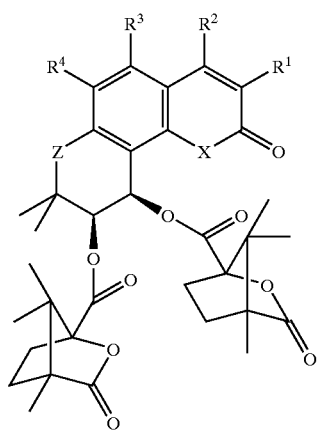

I or a pharmaceutically acceptable salt, ester, or prodrug thereof; wherein $R^1$ and $R^4$ are independently selected from the group consisting of hydrogen, halogen, hydroxy, alkyl, alkoxy, acyloxy, amino, monoalkylamino, dialkylamino, trifluoromethyl, trifluoromethoxy, —CH$_2$CONH-alkyl, and C$_{1-4}$ alkyl substituted with one or more of halogen, trifluoromethyl, cyano, hydroxy, amino, monoalkylamino, or dialkylamino, wherein at least one of $R^1$ or $R^4$ is the substituted C$_{1-4}$ alkyl group;

$R_2$ and $R^3$ are independently selected from the group consisting of hydrogen, halogen, hydroxy, alkyl, alkoxy, acyloxy, amino, monoalkylamino, dialkylamino, trifluoromethyl, trifluoromethoxy, phenyl, and —CH$_2$CONH-alkyl;

X and Z are independently selected from the group consisting of O, S and NH; and where the configurations at 3' and 4' can be (R) or (S).

2. The compound according to claim 1, wherein $R^3$ and $R^4$ are hydrogen, and $R^1$ is a substituted C$_{1-4}$ alkyl group.

3. The compound according to claim 1, wherein $R^1$ and $R^3$ are hydrogen, and $R^4$ is a substituted C$_{1-4}$ alkyl group.

4. The compound according to claim 1, wherein $R^1$ or $R^4$ is a hydroxymethyl or halomethyl group or an ester thereof.

5. The compound according to claim 4, wherein the ester is selected from the group consisting of an alkylcarboxylic acid ester and a dialkylphosphate ester.

6. The compound according to claim 1, wherein at least one of $R^1$ or $R^4$ is —(CH$_2$)$_{1-4}$Y, wherein Y is selected from the group consisting of —O—C(O)—(CH$_2$)$_n$—CO$_2$H; —O—C(O)—(CH$_2$)$_n$—NH$_2$; —O—P(O)(OR)$_2$; and —O—SO$_2$R, wherein R is —(CH$_2$)$_n$—NH$_2$ or —(CH$_2$)$_n$—CO$_2$H and n is an integer from 1 to 10, or a salt or ester thereof.

7. The compound according to claim 6, wherein n is from 2 to 6.

8. The compound according to claim 1, wherein $R^2$ is hydrogen or C$_{1-4}$ alkyl.

9. The compound according to claim 6, wherein $R^2$ is methyl.

10. The compound according to claim 1, wherein the configurations at 3' and 4' are both (R).

11. The compound according to claim 1, wherein the O-camphanoyl group is O-(S)-(−)-camphanoyl.

12. The compound according to claim 1 which is a compound of Formula II:

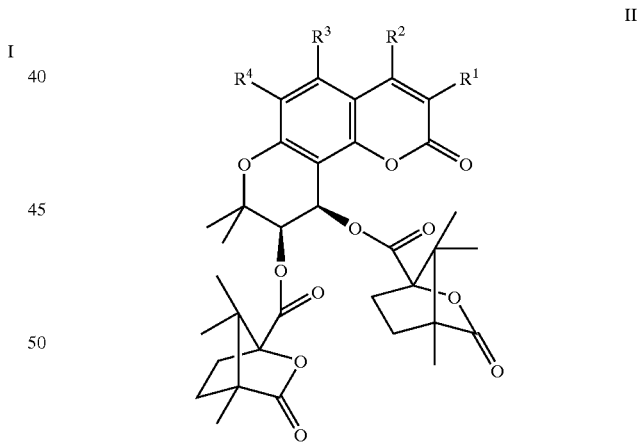

II or a pharmaceutically acceptable salt, ester or prodrug thereof; wherein $R^1$ and $R^4$ are independently selected from the group consisting of hydrogen, halogen, hydroxy, alkoxy, acyloxy, amino, monoalkylamino, dialkylamino, trifluoromethyl, trifluoromethoxy, —CH$_2$CONH-alkyl, and C$_{1-4}$ alkyl substituted with one or more of halogen, trifluoromethyl, cyano, hydroxy, amino, monoalkylamino, or dialkylamino, wherein at least one of $R^1$ or $R^4$ is the substituted C$_{1-4}$ alkyl group;

$R_2$ and $R^3$ are independently selected from the group consisting of hydrogen, halogen, hydroxy, alkoxy, acyloxy, amino, monoalkylamino, dialkylamino, trifluoromethyl, trifluoromethoxy, phenyl, and —$C_2$CONH-alkyl; and where the configurations at 3' and 4' can be (R) or (S).

13. The compound according to claim 12, wherein $R^3$ and $R^4$ are hydrogen, and $R^1$ is a substituted $C_{1-4}$ alkyl group.

14. The compound according to claim 12, wherein $R^1$ and $R^3$ are hydrogen, and $R^4$ is a substituted $C_{1-4}$ alkyl group.

15. The compound according to claim 12, wherein $R^1$ or $R^4$ is a hydroxymethyl or halomethyl group or an ester thereof.

16. The compound according to claim 15, wherein the ester is selected from the group consisting of an alkylcarboxylic acid ester and a dialkylphosphate ester.

17. The compound according to claim 12, wherein at least one of $R^1$ or $R^4$ is —$(CH_2)_{1-4}$Y, wherein Y is selected from the group consisting of —O—C(O)—$(CH_2)_n$—$CO_2$H; —O—C(O)—$(CH_2)_n$—$NH_2$; —O—P(O)(OR)$_2$; and —O—$SO_2$R, wherein R is —$(CH_2)_n$—$NH_2$ or —$(CH_2)_n$—$CO_2$H and n is an integer from 1 to 10, or a salt or ester thereof.

18. The compound according to claim 17, wherein n is from 2 to 6.

19. The compound according to claim 12, wherein $R^2$ is hydrogen or $C_{1-4}$alkyl.

20. The compound according to claim 19, wherein $R^2$ is methyl.

21. The compound according to claim 12, wherein the configurations at 3' and 4' are both (R).

22. The compound according to claim 12, wherein the O-camphanoyl group is O-(S)-(−)-camphanoyl.

23. The compound according to claim 12, wherein said compound is:

(3'R,4'R)-3',4'-di-O-(S)-(−)-camphanoyl-3-bromomethyl-(+)-cis-khellactone;

(3'R,4'R)-3',4'-di-O-(S)-(−)-camphanoyl-3-dibromomethyl-(+)-cis-khellactone;

(3'R,4'R)-3',4'-di-O-(S)-(−)-camphanoyl-3-acetoxymethyl-(+)-cis-khellactone;

(3'R,4'R)-3',4'-di-O-(S)-(−)-camphanoyl-3-hydroxymethyl-(+)-cis-khellactone;

(3'R,4'R)-3',4'-di-O-(S)-(−)-camphanoyl-3-bromomethyl-4-methyl-(+)-cis-khellactone;

(3'R,4'R)-3',4'-di-O-(S)-(−)-camphanoyl-3-acetoxymethyl-4-methyl-(+)-cis-khellactone;

(3'R,4'R)-3',4'-di-O-(S)-(−)-camphanoyl-3-hydroxymethyl-4-methyl-(+)-cis-khellactone;

(3'R,4'R)-3',4'-di-O-(S)-(−)-camphanoyl-6-bromomethyl-(+)-cis-khellactone;

(3'R,4'R)-3',4'-di-O-(S)-(−)-camphanoyl-6-dibromomethyl-4-methyl-(+)-cis-khellactone;

(3'R,4'R)-3',4'-di-O-(S)-(−)-camphanoyl-6-bromomethyl-4-methyl-(+)-cis-khellactone;

(3'R,4'R)-3',4'-di-O-(S)-(−)-camphanoyl-6-acetoxymethyl-4-methyl-(+)-cis-khellactone;

(3'R,4'R)-3',4'-di-O-(S)-(−)-camphanoyl-6-hydroxymethyl-4-methyl-(+)-cis-khellactone;

(3'R,4'R)-3',4'-di-O-(S)-(−)-camphanoyl-6-(dimethylphosphate)-methyl-4-methyl-(+)-cis-khellactone;

(3'R,4'R)-3',4'-di-O-(S)-(−)-camphanoyl-3-aminomethyl-(+)-cis-khellactone;

(3'R,4'R)-3',4'-di-O-(S)-(−)-camphanoyl-6-aminomethyl-4-methyl-(+)-cis-khellactone; and (3'R,4'R)-3',4'-di-O-(S)-(−)-camphanoyl-3-diethylaminomethyl-(+)-cis-khellactone or a pharmaceutically acceptable salt, ester or prodrug thereof.

* * * * *